US012558232B2

(12) United States Patent
Donohoe et al.

(10) Patent No.: US 12,558,232 B2
(45) Date of Patent: Feb. 24, 2026

(54) EXPANDABLE SPINAL FUSION IMPLANTS AND INSERTION DEVICES

(71) Applicant: NuVasive, Inc., San Diego, CA (US)

(72) Inventors: John Donohoe, San Diego, CA (US);
Andrew Wood, San Diego, CA (US);
Adam Carver, San Diego, CA (US);
Nicholas Hilborn, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 17/712,178

(22) Filed: Apr. 3, 2022

(65) Prior Publication Data

US 2022/0313450 A1 Oct. 6, 2022

Related U.S. Application Data

(60) Provisional application No. 63/229,389, filed on Aug. 4, 2021, provisional application No. 63/170,533, filed on Apr. 4, 2021.

(51) Int. Cl.
*A61F 2/44* (2006.01)
*A61F 2/46* (2006.01)
A61F 2/30 (2006.01)

(52) U.S. Cl.
CPC .............. *A61F 2/447* (2013.01); *A61F 2/442* (2013.01); *A61F 2/4611* (2013.01); *A61F 2002/30266* (2013.01); *A61F 2002/30405* (2013.01); *A61F 2002/30484* (2013.01); *A61F 2002/30538* (2013.01)

(58) Field of Classification Search
CPC ...... A61F 2/4455; A61F 2/446; A61F 2/4465; A61F 2/447; A61F 2002/30266; A61F 2002/30556; A61F 2002/30545; A61F 2002/30553
See application file for complete search history.

(56) References Cited

U.S. PATENT DOCUMENTS

| | | | |
|---|---|---|---|
| 5,554,191 | A | 9/1996 | Lahille et al. |
| 5,865,848 | A | 2/1999 | Baker |
| 6,045,579 | A | 4/2000 | Hochshuler et al. |
| 6,136,031 | A | 10/2000 | Middleton |
| 6,176,882 | B1 | 1/2001 | Biedermann et al. |
| 6,395,035 | B2 | 5/2002 | Bresina et al. |
| 6,436,142 | B1 | 8/2002 | Paes et al. |
| 6,443,990 | B1 | 9/2002 | Aebi et al. |
| 6,451,057 | B1 | 9/2002 | Chen et al. |
| 6,719,796 | B2 | 4/2004 | Cohen et al. |
| 6,821,298 | B1 | 11/2004 | Jackson |
| 7,128,760 | B2 | 10/2006 | Michelson |

(Continued)

FOREIGN PATENT DOCUMENTS

| | | |
|---|---|---|
| CN | 100584283 C | 1/2010 |
| EP | 2226039 A1 | 9/2010 |

(Continued)

OTHER PUBLICATIONS

Definition of "align", http://www.thefreedictionary.com/align (Year: 2024).*

(Continued)

*Primary Examiner* — Jan Christopher L Merene

(57) ABSTRACT

This disclosure includes expandable spinal fusion implants, instrumentation, and methods for using the same.

6 Claims, 37 Drawing Sheets

(56) References Cited

U.S. PATENT DOCUMENTS

| | | | |
|---|---|---|---|
| 7,217,291 B2 | 5/2007 | Zucherman et al. |
| 7,763,028 B2 | 7/2010 | Lim et al. |
| 7,819,921 B2 | 10/2010 | Grotz |
| 7,837,734 B2 | 11/2010 | Zucherman et al. |
| 7,985,256 B2 | 7/2011 | Grotz et al. |
| 8,105,382 B2 | 1/2012 | Olmos et al. |
| 8,398,713 B2 | 3/2013 | Weiman |
| 8,435,298 B2 | 5/2013 | Weiman |
| 8,454,617 B2 | 6/2013 | Schaller et al. |
| 8,465,547 B2 | 6/2013 | Melkent et al. |
| 8,491,659 B2 | 7/2013 | Weiman |
| 8,496,706 B2 | 7/2013 | Ragab et al. |
| 8,568,481 B2 | 10/2013 | Olmos et al. |
| 8,628,578 B2 | 1/2014 | Miller et al. |
| 8,632,595 B2 | 1/2014 | Weiman |
| 8,679,161 B2 | 3/2014 | Malandain et al. |
| 8,795,366 B2 | 8/2014 | Varela |
| 8,845,731 B2 | 9/2014 | Weiman |
| 8,845,732 B2 | 9/2014 | Weiman |
| 8,845,734 B2 | 9/2014 | Weiman |
| 8,894,711 B2 | 11/2014 | Varela |
| 8,894,712 B2 | 11/2014 | Varela |
| 8,940,049 B1 | 1/2015 | Jimenez et al. |
| 9,039,771 B2 | 5/2015 | Glerum et al. |
| 9,125,757 B2 | 9/2015 | Weiman |
| 9,220,610 B2 | 12/2015 | Chen |
| 9,233,007 B2 | 1/2016 | Sungarian et al. |
| 9,314,348 B2 | 4/2016 | Emstad |
| 9,320,610 B2 | 4/2016 | Alheidt et al. |
| 9,358,129 B2 | 6/2016 | Weiman |
| 9,364,339 B2 | 6/2016 | Mayer |
| 9,370,434 B2 | 6/2016 | Weiman |
| 9,402,739 B2 | 8/2016 | Weiman et al. |
| 9,445,919 B2 | 9/2016 | Palmatier et al. |
| 9,486,328 B2 | 11/2016 | Jimenez et al. |
| 9,492,288 B2 | 11/2016 | Wagner et al. |
| 9,522,070 B2 | 12/2016 | Flower et al. |
| 9,561,116 B2 | 2/2017 | Weiman et al. |
| 9,585,766 B2 | 3/2017 | Robinson |
| 9,585,767 B2 | 3/2017 | Robinson |
| 9,622,878 B2 | 4/2017 | Grotz |
| 9,662,224 B2 | 5/2017 | Weiman et al. |
| 9,668,876 B2 | 6/2017 | Blain et al. |
| 9,668,879 B2 | 6/2017 | Jimenez et al. |
| 9,713,536 B2 | 7/2017 | Foley et al. |
| 9,717,601 B2 | 8/2017 | Miller |
| 9,750,618 B1 | 9/2017 | Daffinson et al. |
| 9,795,493 B1 | 10/2017 | Bannigan |
| 9,801,733 B2 | 10/2017 | Wolters et al. |
| 9,801,734 B1 | 10/2017 | Stein et al. |
| 9,839,528 B2 | 12/2017 | Weiman et al. |
| 9,855,151 B2 | 1/2018 | Weiman |
| 9,861,494 B2 | 1/2018 | Grotz |
| 9,872,778 B2 | 1/2018 | Grotz |
| 9,931,226 B2 | 4/2018 | Kurtaliaj et al. |
| 9,956,087 B2 | 5/2018 | Seifert et al. |
| 9,962,270 B2 | 5/2018 | Alheidt et al. |
| 9,962,272 B1 | 5/2018 | Daffinson et al. |
| 9,987,144 B2 | 6/2018 | Seifert et al. |
| 9,999,515 B1 | 6/2018 | Grotz |
| 10,022,239 B1 | 7/2018 | Lentner et al. |
| 10,034,765 B2 | 7/2018 | Blain et al. |
| 10,034,769 B2 | 7/2018 | Baynham |
| 10,039,650 B2 | 8/2018 | Amborne et al. |
| 10,052,214 B2 | 8/2018 | Jimenez et al. |
| 10,076,423 B2 | 9/2018 | Miller et al. |
| 10,085,846 B2 | 10/2018 | Grotz |
| 10,098,757 B2 | 10/2018 | Logan et al. |
| 10,111,758 B2 | 10/2018 | Robinson |
| 10,154,911 B2 | 12/2018 | Predick et al. |
| 10,154,914 B2 | 12/2018 | Robinson |
| 10,172,718 B2 | 1/2019 | Wolters et al. |
| 10,195,050 B2 | 2/2019 | Palmatier et al. |
| 10,226,356 B2 | 3/2019 | Grotz |
| 10,238,503 B2 | 3/2019 | Branch et al. |
| 10,278,830 B1 | 5/2019 | Walker et al. |
| 10,278,831 B2 | 5/2019 | Sandul |
| 10,285,819 B2 | 5/2019 | Greenhalgh |
| 10,285,820 B2 | 5/2019 | Greenhalgh |
| 10,285,824 B2 | 5/2019 | Robinson |
| 10,292,828 B2 | 5/2019 | Greenhalgh |
| 10,292,830 B2 | 5/2019 | McLuen et al. |
| 10,299,934 B2 | 5/2019 | Seifert et al. |
| 10,314,719 B2 | 6/2019 | Hessler et al. |
| 10,322,011 B2 | 6/2019 | Baynham |
| 10,327,917 B2 | 6/2019 | Glerum et al. |
| 10,350,081 B2 | 7/2019 | Seifert et al. |
| 10,350,084 B1 | 7/2019 | Lin et al. |
| 10,350,085 B2 | 7/2019 | Glerum et al. |
| 10,363,142 B2 | 7/2019 | McClintock et al. |
| 10,369,004 B2 | 8/2019 | Faulhaber |
| 10,369,010 B2 | 8/2019 | Robinson et al. |
| 10,376,377 B2 | 8/2019 | Seifert et al. |
| 10,383,741 B2 | 8/2019 | Butler et al. |
| 10,390,960 B2 | 8/2019 | Bannigan et al. |
| 10,390,962 B2 | 8/2019 | Weiman |
| 10,390,963 B2 | 8/2019 | Olmos et al. |
| 10,398,563 B2 | 9/2019 | Engstrom |
| 10,398,566 B2 | 9/2019 | Olmos et al. |
| 10,398,567 B2 | 9/2019 | Robinson |
| 10,413,421 B2 | 9/2019 | Arnold et al. |
| 10,413,422 B2 | 9/2019 | Flower et al. |
| 10,420,654 B2 | 9/2019 | Logan et al. |
| 10,426,632 B2 | 10/2019 | Butler et al. |
| 10,441,430 B2 | 10/2019 | Ludwig et al. |
| 10,449,056 B2 | 10/2019 | Cain |
| 10,492,924 B2 | 12/2019 | Stein et al. |
| 10,500,064 B2 | 12/2019 | Robinson |
| 10,507,116 B2 | 12/2019 | Shoshtaev |
| 10,512,550 B2 | 12/2019 | Bechtel et al. |
| 10,524,924 B2 | 1/2020 | Davenport et al. |
| 10,531,964 B2 | 1/2020 | Miller et al. |
| 10,575,964 B2 | 3/2020 | Robinson |
| 10,575,966 B2 | 3/2020 | Logan et al. |
| 10,583,015 B2 | 3/2020 | Olmos et al. |
| 10,610,376 B2 | 4/2020 | Kuyler et al. |
| 10,610,377 B2 | 4/2020 | Baynham |
| 10,617,533 B2 | 4/2020 | Glerum et al. |
| 10,624,761 B2 | 4/2020 | Davenport et al. |
| 10,631,998 B2 | 4/2020 | Wu et al. |
| 10,639,166 B2 | 5/2020 | Weiman et al. |
| 10,646,351 B2 | 5/2020 | Blain et al. |
| 10,667,927 B2 | 6/2020 | Lamborne et al. |
| 10,682,239 B2 | 6/2020 | Hsu et al. |
| 10,682,241 B2 | 6/2020 | Glerum et al. |
| 10,687,963 B2 | 6/2020 | Jimenez et al. |
| 10,869,768 B2 * | 12/2020 | Weiman ................. A61F 2/447 |
| 10,973,650 B2 | 4/2021 | Stein |
| 11,234,833 B2 | 2/2022 | Brotman et al. |
| 11,273,047 B2 | 3/2022 | Besaw et al. |
| 2002/0045945 A1 | 4/2002 | Liu et al. |
| 2004/0087947 A1 | 5/2004 | Lim et al. |
| 2006/0247781 A1 | 11/2006 | Francis et al. |
| 2009/0222100 A1 | 9/2009 | Cipoletti et al. |
| 2009/0292361 A1 | 11/2009 | Lopez |
| 2010/0145455 A1 | 6/2010 | Simpson et al. |
| 2011/0015742 A1 | 1/2011 | Hong |
| 2011/0112644 A1 | 5/2011 | Zilberstein et al. |
| 2011/0160861 A1 | 6/2011 | Jimenez et al. |
| 2012/0059475 A1 * | 3/2012 | Weiman ................. A61F 2/447 |
| | | | 623/17.16 |
| 2012/0271422 A1 * | 10/2012 | Miller ..................... A61F 2/447 |
| | | | 623/17.16 |
| 2013/0231747 A1 | 9/2013 | Olmos et al. |
| 2014/0094856 A1 * | 4/2014 | Sinha ................. A61B 17/8052 |
| | | | 606/291 |
| 2014/0236296 A1 | 8/2014 | Wagner et al. |
| 2014/0236297 A1 | 8/2014 | Iott et al. |
| 2015/0272743 A1 | 10/2015 | Jimenez et al. |
| 2015/0374508 A1 | 12/2015 | Sandul |
| 2016/0022434 A1 | 1/2016 | Robinson |
| 2016/0089247 A1 * | 3/2016 | Nichols ................. A61F 2/4455 |
| | | | 623/17.16 |
| 2016/0166396 A1 | 6/2016 | McClintock |

(56) References Cited

U.S. PATENT DOCUMENTS

| | | |
|---|---|---|
| 2016/0256291 A1 | 9/2016 | Miller |
| 2017/0042695 A1* | 2/2017 | Foley .................. A61F 2/4601 |
| 2017/0105844 A1 | 4/2017 | Kuyler et al. |
| 2017/0112630 A1 | 4/2017 | Kuyler et al. |
| 2017/0119542 A1 | 5/2017 | Logan et al. |
| 2017/0135824 A1 | 5/2017 | Suddaby et al. |
| 2017/0143507 A1 | 5/2017 | Flower et al. |
| 2017/0151065 A1 | 6/2017 | Warren et al. |
| 2017/0216049 A1 | 8/2017 | Grotz |
| 2017/0224504 A1 | 8/2017 | Butler et al. |
| 2017/0224505 A1 | 8/2017 | Butler et al. |
| 2017/0231780 A1 | 8/2017 | D'Urso |
| 2017/0281358 A1 | 10/2017 | Wagner et al. |
| 2017/0290674 A1 | 10/2017 | Olmos et al. |
| 2017/0290675 A1 | 10/2017 | Olmos et al. |
| 2017/0290676 A1 | 10/2017 | Olmos et al. |
| 2017/0290677 A1 | 10/2017 | Olmos et al. |
| 2017/0290678 A1 | 10/2017 | Olmos et al. |
| 2017/0333198 A1 | 11/2017 | Robinson |
| 2018/0036138 A1 | 2/2018 | Robinson |
| 2018/0049785 A1* | 2/2018 | Langdale .......... A61B 17/8042 |
| 2018/0064551 A1 | 3/2018 | Stein et al. |
| 2018/0147065 A1 | 5/2018 | Daffinson et al. |
| 2018/0147066 A1 | 5/2018 | Daffinson et al. |
| 2018/0161171 A1 | 6/2018 | Frasier et al. |
| 2018/0161175 A1 | 6/2018 | Frasier et al. |
| 2018/0193160 A1 | 7/2018 | Hsu et al. |
| 2018/0296361 A1 | 10/2018 | Butler et al. |
| 2018/0303625 A1 | 10/2018 | Alheidt et al. |
| 2018/0333273 A1 | 11/2018 | Blain et al. |
| 2018/0360615 A1 | 12/2018 | Miller et al. |
| 2019/0008649 A1 | 1/2019 | Logan et al. |
| 2019/0008657 A1 | 1/2019 | Amborne et al. |
| 2019/0021868 A1 | 1/2019 | Ludwig et al. |
| 2019/0021870 A1 | 1/2019 | Jimenez et al. |
| 2019/0021872 A1 | 1/2019 | Robinson |
| 2019/0133780 A1 | 5/2019 | Matthews et al. |
| 2019/0133788 A1 | 5/2019 | Weiman et al. |
| 2019/0142602 A1 | 5/2019 | Olmos et al. |
| 2019/0151110 A1 | 5/2019 | Faulhaber |
| 2019/0201209 A1 | 7/2019 | Branch et al. |
| 2019/0231552 A1 | 8/2019 | Sandul |
| 2019/0240039 A1 | 8/2019 | Walker et al. |
| 2019/0240043 A1 | 8/2019 | Greenhalgh |
| 2019/0274837 A1 | 9/2019 | Eisen et al. |
| 2019/0274838 A1 | 9/2019 | Manwill et al. |
| 2019/0290447 A1 | 9/2019 | Stein |
| 2019/0314168 A1 | 10/2019 | Faulhaber |
| 2019/0321190 A1 | 10/2019 | Wagner et al. |
| 2019/0321191 A1 | 10/2019 | Glerum et al. |
| 2019/0321198 A1 | 10/2019 | Glerum et al. |
| 2019/0328540 A1 | 10/2019 | Seifert et al. |
| 2019/0336301 A1 | 11/2019 | Engstrom |
| 2019/0336302 A1 | 11/2019 | Seifert et al. |
| 2019/0358051 A1 | 11/2019 | Flower et al. |
| 2019/0374348 A1 | 12/2019 | Butler et al. |
| 2019/0388232 A1* | 12/2019 | Purcell .................. A61F 2/4455 |
| 2020/0008951 A1 | 1/2020 | McClintock et al. |
| 2020/0030114 A1 | 1/2020 | Cain |
| 2020/0085586 A1 | 3/2020 | Ludwig et al. |
| 2020/0093607 A1 | 3/2020 | Davenport et al. |
| 2020/0093609 A1 | 3/2020 | Shoshtaev |
| 2020/0100904 A1 | 4/2020 | Stein et al. |
| 2020/0113706 A1 | 4/2020 | Robinson |
| 2020/0129306 A1 | 4/2020 | Miller et al. |
| 2020/0129307 A1 | 4/2020 | Hunziker et al. |
| 2021/0045891 A1* | 2/2021 | Rogers .................. A61F 2/4425 |
| 2023/0165687 A1* | 6/2023 | Barrus .................. A61F 2/4455 623/17.11 |
| 2023/0190490 A1* | 6/2023 | Corrao, Jr. .............. A61F 2/447 623/17.11 |
| 2023/0285163 A1* | 9/2023 | Reimels .................. A61F 2/447 623/17.11 |

FOREIGN PATENT DOCUMENTS

| | | | | |
|---|---|---|---|---|
| EP | 2764851 A1 * | 8/2014 | ............ | A61F 2/446 |
| JP | 2000210315 A | 8/2000 | | |
| JP | 2008054710 A | 3/2008 | | |
| KR | 100900991 B1 | 6/2009 | | |
| KR | 100905962 B1 | 7/2009 | | |
| RU | 2460499 C2 | 9/2012 | | |
| WO | 2016/069796 A1 | 5/2016 | | |
| WO | 2017/027277 A1 | 2/2017 | | |

OTHER PUBLICATIONS

Definition for "abut", https://www.thefreedictionary.com/abut (Year: 2025).*

International Search Report and Written Opinion, International Application No. PCT/US2022/023222, dated Sep. 8, 2022, 15 pages.

* cited by examiner

200

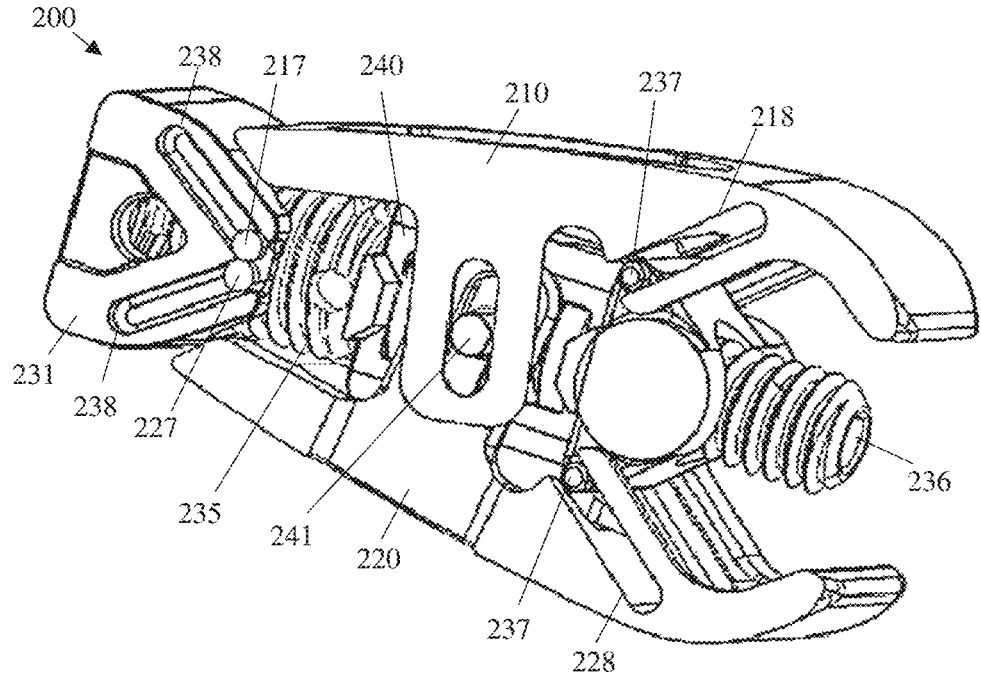
FIG. 15
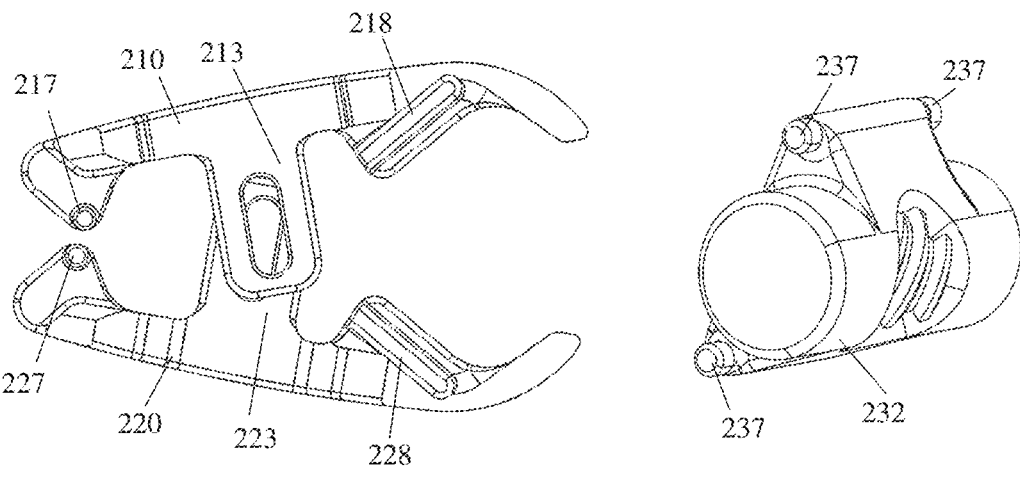
FIG. 16                    FIG. 17

EXPANDABLE SPINAL FUSION IMPLANTS AND INSERTION DEVICES

CROSS REFERENCE TO RELATED APPLICATIONS

The present patent application claims priority to U.S. Provisional Patent Application No. 63/170,533, filed on Apr. 4, 2021, and to U.S. Provisional Patent Application No. 63/229,389, filed on Aug. 4, 2021.

BACKGROUND OF THE INVENTION

Field of the Invention

The present disclosure relates generally to medical implants and associated instrumentation, and more particularly to expandable spinal fusion implants and insertion devices.

Description of the Related Art

Back problems are one of the most common and debilitating medical occurrences. In the United States alone, over 500,000 spinal lumbar and cervical fusion procedures are performed each year. One of the causes of back pain and disability results from the rupture or degeneration of one or more intervertebral discs in the spine.

Surgical procedures are commonly performed to correct problems with displaced, damaged, or degenerated intervertebral discs due to trauma, disease, or aging. Generally, spinal fusion procedures involve removing some or all of the diseased or damaged disc, and inserting one or more intervertebral implants into the resulting disc space. Anterior lumbar interbody fusion (ALIF) and lateral lumbar interbody fusion procedures are two of the techniques that spine surgeons use to access the portions of the spine to be repaired or replaced.

Replacement of injured or deteriorated spinal bone with artificial implants involves knowledge of the mechanisms of the inherent stresses on the spine, as well as the biological properties of the body in response to the devices. Further, the size, configuration, and placement of an artificial implant involves precision positioning and handling by a skilled surgeon.

SUMMARY OF THE INVENTION

This disclosure includes expandable spinal fusion implants, instrumentation, and methods for using the same.

In some embodiments, an expandable spinal fusion implant includes: a first endplate, a second endplate, and an actuator configured to change a dimension of the expandable spinal fusion implant. In some embodiments, the dimension of the expandable spinal fusion implant to be changed may include at least one of: a height, a width, a length, and an angulation of the first endplate with respect to the second endplate, for example, lordosis angle.

In some embodiments, an expandable spinal fusion implant includes: a first endplate, a second endplate, and an actuator. The actuator may include a first lead screw having a length, the first lead screw rotatably disposed between the first endplate and the second endplate, and a wedge configured to translate along the length of the first lead screw as the first lead screw is rotated. Communication between the wedge and the first endplate and the second endplate may change a dimension of the expandable implant.

In some embodiments, an expandable spinal fusion implant includes: a first endplate, a second endplate, and an actuator. Both the first endplate and the second endplate may include at least one wedge contact surface. The actuator includes a first lead screw, a first wedge configured to translate along the length of the first lead screw as the first lead screw is rotated, a second lead screw, and a second wedge configured to translate along the length of the second lead screw as the second lead screw is rotated, wherein the first lead screw is configured to rotate independently of the second lead screw and communication between the first wedge and the second wedge with the first endplate and the second endplate may change a dimension of the expandable implant.

In some embodiments, an expandable spinal fusion implant includes: a first endplate having a first barrel contact surface, a second endplate having a second barrel contact surface, a first lead screw having a length, and a threaded barrel configured to translate along the length of the lead screw as the lead screw is rotated. A surface of the threaded barrel is configured to communicate with the first barrel contact surface of the first endplate and the second barrel contact surface of the second endplate and configured to move the first endplate relative to the second endplate to change a dimension of the expandable spinal fusion implant.

In some embodiments, an expandable spinal fusion implant includes: a first endplate having a first linkage, a first barrel contact surface, and a first ramp and a second endplate having a second linkage, a second barrel contact surface and a second ramp, a first lead screw coupled to a second lead screw by a coupler, the first lead screw configured to rotate independently of the second lead screw, a threaded barrel configured to translate along a length of the first lead screw as the first lead screw is rotated, the threaded barrel configured to communicate with the first barrel contact surface of the first endplate and the second barrel contact surface of the second endplate to displace the first endplate relative to the second endplate. This displacement of the first endplate relative to the second endplate changes a dimension of the expandable spinal fusion implant. A second threaded nut is configured to translate along the second lead screw as the second lead screw is rotated, the second threaded nut having a wedge configured to communicate with the first ramp of the first endplate and the second ramp of the second endplate to displace the first endplate relative to the second endplate to change the dimension of the expandable spinal fusion implant.

In some embodiments, an expandable spinal fusion implant includes: a first endplate having a first linkage, a first barrel contact surface, and a first ramp and a second endplate having a second linkage, a second barrel contact surface and a second ramp, a first lead screw coupled to a second lead screw by a coupler disposed between the first endplate and the second endplate, wherein the first lead screw is configured to rotate independently of the second lead screw, and wherein the coupler is configured to moveably connect the first endplate and the second endplate, a threaded barrel having a substantially circular profile, configured to translate along a length of the second lead screw as the second lead screw is rotated, the threaded barrel configured to communicate with the first barrel contact surface of the first endplate and the second barrel contact surface of the second endplate to displace the first endplate relative to the second endplate to change a dimension of the expandable spinal fusion implant; and a wedge configured to translate along the first lead screw as the first lead screw is rotated, the second wedge having a wedge configured to communicate with the first ramp of the first endplate and the second ramp of the second endplate to displace the first endplate relative to the second endplate to change the dimension of the expandable spinal fusion implant.

In some embodiments a surgical instrument includes: an inserter configured to deliver an expandable spinal fusion implant to an intervertebral space of a patient and an expansion driver configured to adjust the expandable spinal fusion implant in situ.

In some embodiments a surgical instrument includes: an inserter, an expansion driver and an indicator handle configured to communicate an amount of adjustment of the expandable implant to a user.

In some embodiments a surgical instrument includes: an inserter having a pair of arms configured to communicate with an expandable spinal fusion implant to removably secure the expandable spinal fusion implant to the inserter with the inserter configured to deliver the expandable spinal fusion implant to an intervertebral space of a patient, an expansion driver having a clutch mechanism configured to selectively adjust the expandable spinal fusion implant in situ, and an indicator handle having at least one display configured to communicate an amount of adjustment of the expandable implant to a user, the amount of adjustment including at least one of a height and an angle of lordosis of the expandable spinal fusion implant.

In some embodiments a surgical instrument includes: an inserter, an expansion driver and an indicator handle.

BRIEF DESCRIPTION OF THE DRAWINGS

These and other features may be further understood by those with skill in the art upon a review of the appended drawings, wherein:

FIG. 15 shows a perspective sectional view of the expandable spinal fusion implant in accordance with the embodiment of FIG. 10;

FIG. 16 shows a sectional side view of a first endplate and a second endplate;

FIG. 17 shows a perspective view of a threaded barrel;

DETAILED DESCRIPTION

Figure 1:
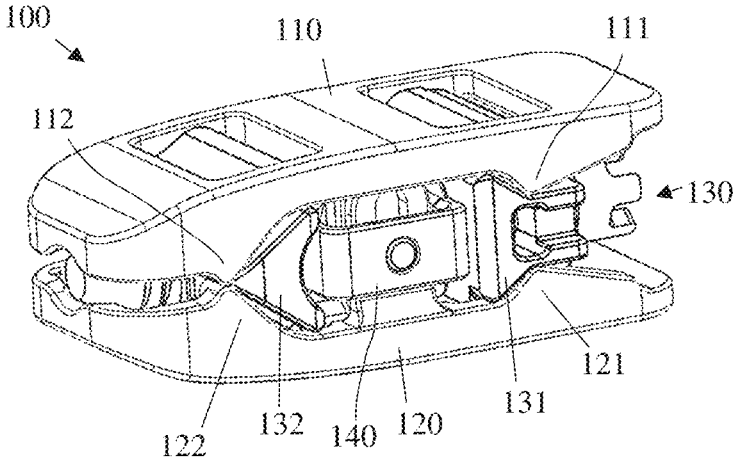
FIG. 1 shows a front perspective view of an expandable spinal fusion implant in accordance with an embodiment of the disclosure.
Figure 2:
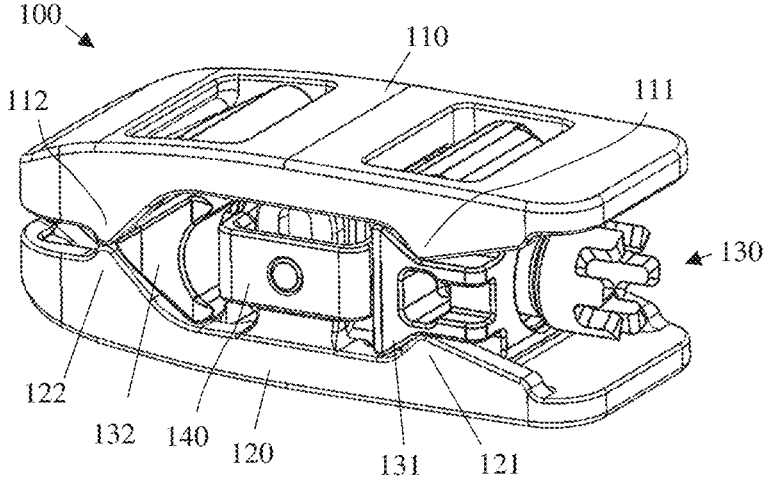
FIG. 2 shows a rear perspective view of an expandable spinal fusion implant in accordance with the embodiment of FIG. 1.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary sill in the art having the benefit of this disclosure. The expandable spinal fusion implant and related methods disclosed herein boast a variety of inventive features and components that warrant patent protection, both individually and in combination.

In general, the expandable spinal fusion implants described in this document include upper and lower endplates and an actuator with at least a portion of the actuator disposed between the upper endplate and lower endplate and configured to change a dimension of the spinal fusion implant. The expandable spinal fusion implant is designed to be inserted into the disc space between adjacent vertebral bodies from a lateral or posterior approach. The implant may be made of any suitable, biocompatible material or combination of materials. For example, the implant components may be metal, poly ether ether ketone (PEEK), or a combination of the metal and PEEK. The implant is configured to be inserted into the disc space in a collapsed state and upon being seated in a desired location within the disc space, the distal end of the implant is expanded in height to create an implant with a lordotic angle (i.e., the anterior height of the implant is greater than the posterior height of the implant, thereby restoring a more natural lordotic curvature of the particular segment of the lumbar spine). The expansion is accomplished by engaging the actuator with an expansion driver to activate the actuator and cause the translating wedge and/or threaded barrel to move between the implants in a distal direction.

Expandable spinal fusion implants may be adjusted to a certain height and to a particular lordosis angle, the selection of which may be influenced by, inter alia, the needs or requirements of the patient, or the target procedure of a surgeon. The implants may incorporate various features to accommodate and/or promote spinal fusion.

Now turning to the drawings, FIGS. 1-9 show various views of an expandable spinal fusion implant 100 in accordance with a first embodiment. The expandable implant includes a first endplate 110 and a second endplate 120. The first endplate has a first ramp 111 and a second ramp 112. The second endplate also has a first ramp 121 and a second ramp 122.

The actuator 130 includes a first wedge 131, a second wedge 132, and a first lead screw 135, which may be rotatable one of independently or simultaneously relative to a second lead screw 136. The first wedge 131 is configured to travel along the length of the first lead screw 135 as the first lead screw 135 is rotated. Similarly, the second wedge 132 is configured to travel along the length of the second lead screw 136, as the second lead screw 136 is rotated. As one with skill in the art may appreciate, the first lead screw 135 may be coupled to the second lead screw 136 by a coupler 140, such that the first lead screw 135 can be rotated independently from the second lead screw 136.

Figures 3A, 3B, 4A, 4B, 5A, 5B:
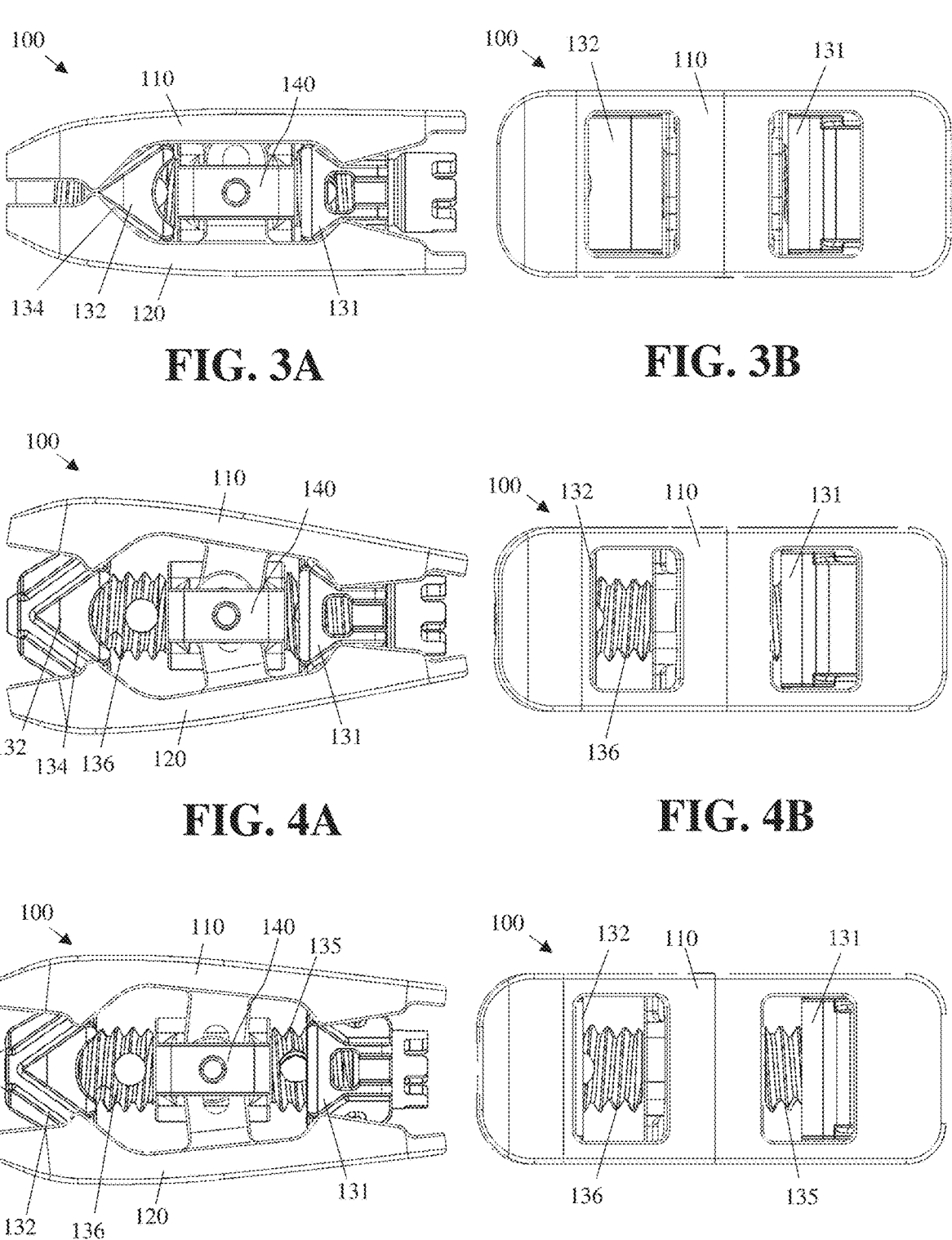
FIG. 3A shows a side view of the expandable spinal fusion implant adjusted to a minimum height.
FIG. 3B shows a top view of the expandable spinal fusion implant adjusted to a minimum height and shows the relative locations of the wedges.
FIG. 4A shows a side view of the expandable spinal fusion implant adjusted to an exemplary angle of lordosis.
FIG. 4B shows a top view of the expandable spinal fusion implant adjusted to the exemplary angle of lordosis and shows the relative locations of the wedges.
FIG. 5A shows a side view of the expandable spinal fusion implant adjusted to a maximum height.
FIG. 5B shows a top view of the expandable spinal fusion implant adjusted to a maximum height and shows the relative locations of the wedges.

FIGS. 3A-5B illustrate a range of possible adjustments of expandable spinal fusion implant 100. FIG. 3A shows expandable spinal fusion implant 100 adjusted to a minimum height. FIG. 3B provides a top view of expandable spinal fusion implant 100 in the same configuration, including the relative positions of first wedge 131 and second wedge 132.

As second lead screw 136 is rotated, second wedge 132 will travel along the length of second lead screw 136. As second wedge 132 travels, a wedge surface 134 will push on second ramp 112 of first endplate 110 and second ramp 122 of second endplate 120, changing an angle between first endplate 110 and second endplate 120 (compare FIG. 3A with FIG. 4A).

Similarly, rotation of first lead screw 135 will move first wedge 131 along the length of first lead screw 135. As first wedge 131 travels, the wedge surface 133 will push on first ramp 111 of first endplate 110 and first ramp 121 of second endplate 120, changing an angle between first endplate 110 and second endplate 120, thereby effectively changing the height from height h to height h' (compare FIG. 3A with FIG. 5A).

As one with skill in the art may appreciate, any amount of adjustment of either of the first lead screw or the second lead screw will result in a change in a dimension of the expandable implant. A surgeon can use this functionality to provide any range of adjustment, and with this in mind the implant can be manufactured and dimensioned to provide a range of adjustments according to patient size, lordosis requirements, etc.

Figure 6:
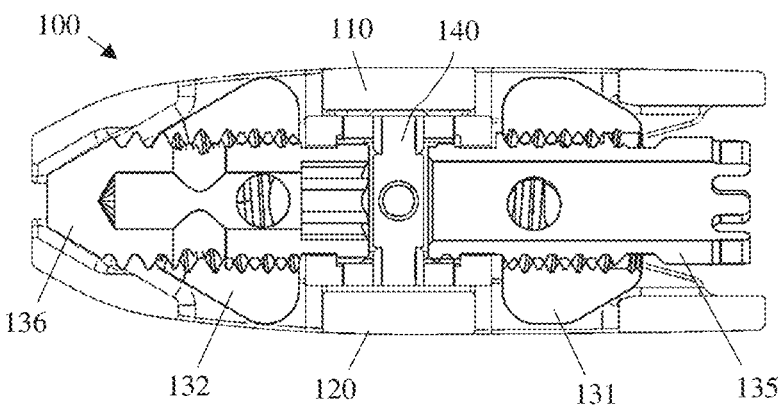
FIG. 6 shows a cross sectional side view of the expandable spinal fusion implant adjusted to a minimum height.
Figure 7:
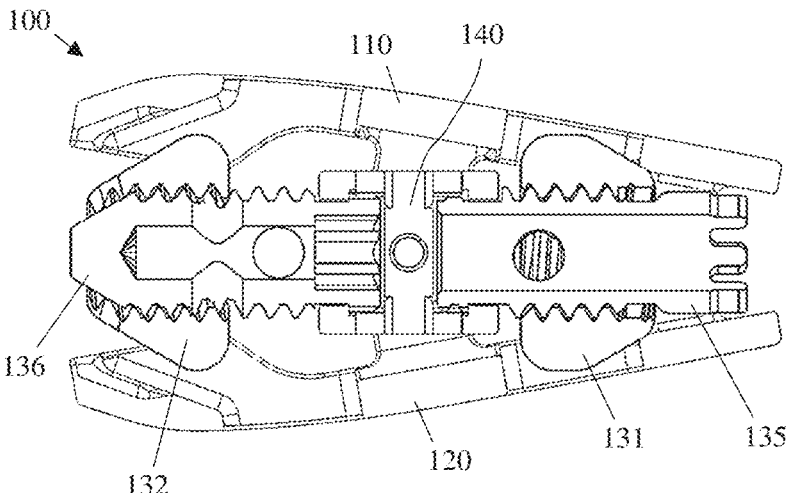
FIG. 7 shows a cross sectional side view of the expandable spinal fusion implant adjusted to an exemplary angle of lordosis.
Figure 8:
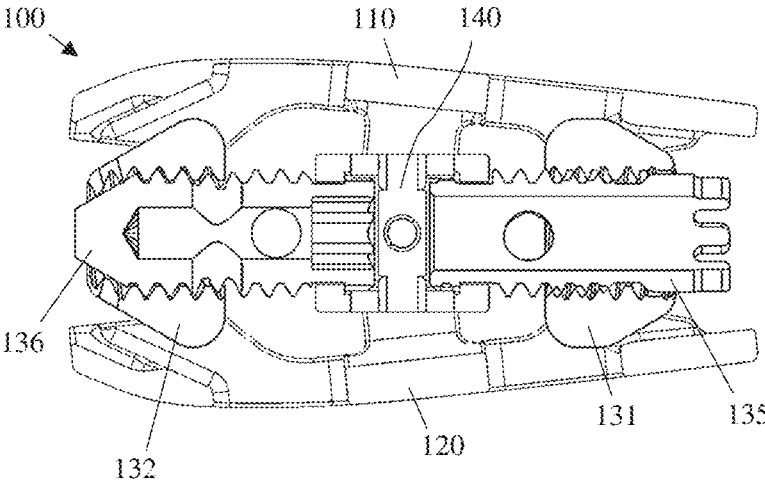
FIG. 8 shows a cross sectional side view of the expandable spinal fusion implant adjusted to a maximum height.

FIGS. 6-8 show cross sectional side views of the expandable spinal fusion implant 100 adjusted to various settings. Expandable spinal fusion implant 100 includes a first endplate 110, a second endplate 120, a first wedge 131, a second wedge 132, and an actuator 130 including a first lead screw 135 rotatably connected to a second lead screw 136. In the illustrated embodiment, first lead screw 135 is rotatably coupled to second lead screw 136 by a coupler 140. The coupler 140 allows first lead screw 135 to be rotated independently of second lead screw 136. This dynamic coupling allows for both independent and simultaneous adjustment of expandable implant 100. Rotating first lead screw 135 in a direction opposite from second lead screw 136 may allow first wedge 131 to travel in an opposite direction of second wedge 132. In some embodiments this may increase the height h without changing the angle between first endplate 110 and second endplate 120. Additionally, moving only one of first wedge 131 and second wedge 132 will change an angle between first endplate 110 and second endplate 120.

Figure 9:
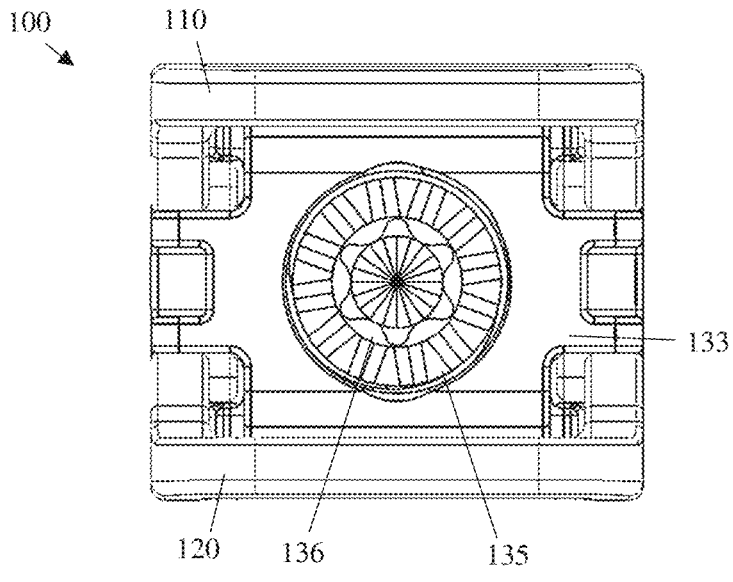
FIG. 9 shows a rear view of the expandable spinal fusion implant.
Figure 10:
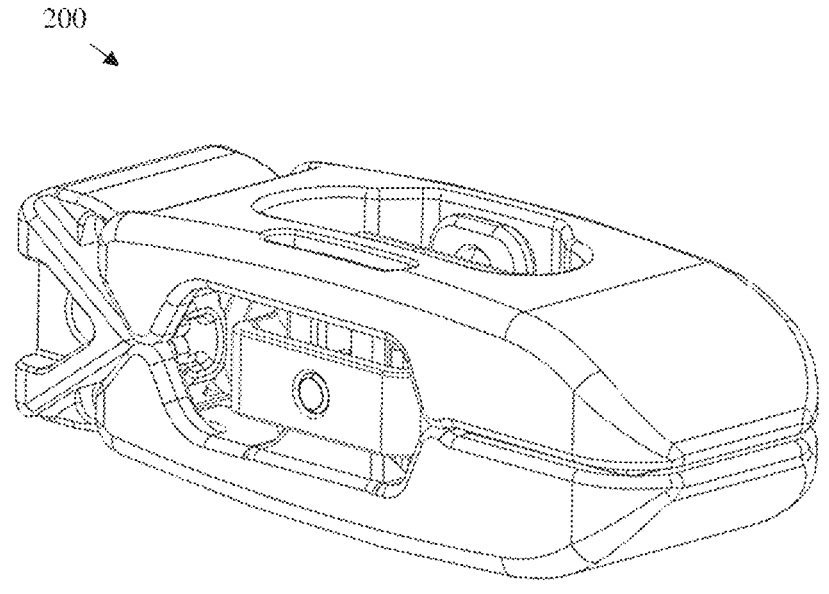
FIG. 10 shows a perspective view of an expandable spinal fusion implant in accordance with a embodiment of the disclosure.

FIG. 9 shows a rear view of expandable spinal fusion implant 100. In particular, a first adjustment head of first lead screw 135 and a second adjustment head of second drive screw 136 are illustrated. In this embodiment, a portion of first lead screw 135 is hollow (see FIGS. 6-8), such that an insertion instrument (e.g., one or more of an inserter, an expansion driver, etc.) can be inserted through first lead screw 135 to rotate second lead screw 136. In some embodiments the insertion instrument has two drivers, a first driver configured to rotate first lead screw 135, and a second driver configured to rotate second lead screw 136 independently or synchronously to adjust expandable spinal fusion implant 100 in situ.

In some embodiments, the lead screw may be a screw or may be formed from one or more threaded portions. In some embodiments first lead screw 135 and second lead screw 136 may alternatively be a single monolithic lead screw. The lead screw may include a first set of threads and a second set of threads. The first set of threads may be opposite the second set of threads such that as the lead screw is rotated, the wedge travels in the opposite direction along the lead screw as the second wedge, thereby changing only the height of the expandable spinal fusion implant.

In some embodiments, first endplate 110 and second endplate 120 may include ramps configured to communicate with wedges as they are translated. In other embodiments first endplate 110 and second endplate 120 may include tabs or protruding elements configured to communicate with the wedges as the wedges move along the length of the lead screws. The wedges may include ramps and/or wedge surfaces, and may be substantially wedge shaped. The wedges move the endplates 110, 120 to adjust a dimension of the expandable implant 100.

First endplate 110 and second endplate 120 may further include slotted tabs. In some embodiments first endplate 110 may be coupled to second endplate 120 by the slotted tabs. In some embodiments, coupler 140 may rotatably connect the first threaded portion to the second threaded portion and moveably attach first endplate 110 to second endplate 120, thereby holding expandable spinal fusion implant 100 together while allowing first endplate 110 to pivot relative to second endplate 120 and allow for angular adjustment, e.g., adjustment of the lordosis angle.

In some embodiments, expandable spinal fusion implant 100 or individual components thereof may be made out of PEEK, porous PEEK, titanium, or any other material commonly used in medical implants. Expandable spinal fusion implant 100 or individual components thereof may be made using additive manufacturing techniques or any other process known.

Turning to FIGS. 10-17, an expandable spinal fusion implant 200 is shown in accordance with a second embodiment. As shown, implant 200 may include: a first endplate 210 having a first barrel contact surface 212, and a second endplate 220 having a second barrel contact surface 222. A first lead screw 235, having a particular length, is provided as shown in, e.g., FIGS. 11-15. A wedge 231 may be configured to translate along the length of first lead screw 235 as first lead screw 235 is rotated. A second lead screw 236 having a particular length and a threaded barrel 232 may be configured to translate along the length of second lead screw 236 as second lead screw 236 is rotated. A surface of threaded barrel 232 is configured to communicate with first barrel contact surface 212 of first endplate 210 and second barrel contact surface 222 of second endplate 220 to move first endplate 210 relative to second endplate 220 and change a dimension of expandable spinal fusion implant 200.

In the illustrated embodiment, first lead screw 235 is movable independently from, and/or simultaneously with second lead screw 236, with first lead screw 235 and second lead screw 236 being configured to be rotated independently. At least a portion of the actuator is disposed between first endplate 210 and second endplate 220.

Threaded barrel 232 is configured to translate along the length of second lead screw 236 as second lead screw 236 is rotated, and wedge 231 is configured to translate along the length of first lead screw 235 as first lead screw 235 is rotated.

Threaded barrel 232 includes a substantially circular endplate contact surface configured to communicate with first barrel contact surface 212 of first endplate 210 and second barrel contact surface 222 of second endplate 220 as threaded barrel 232 is translated along the length of second lead screw 236.

Wedge 231 is configured to translate along the length of first lead screw 235 as first lead screw 235 is rotated. First endplate 210 includes first ramp 211, configured to communicate with wedge 231. Second endplate 220 similarly includes second ramp 221 configured to communicate with wedge 231. First endplate 210 and second endplate 220 include linkages 213, 223 configured to communicate with coupler 240 to moveably secure first endplate 210 relative to second endplate 220.

The dimension of the expandable spinal fusion implant 200 changed by the foregoing movements may include a height and/or an angle between first endplate 210 and second endplate 220.

Figure 11:
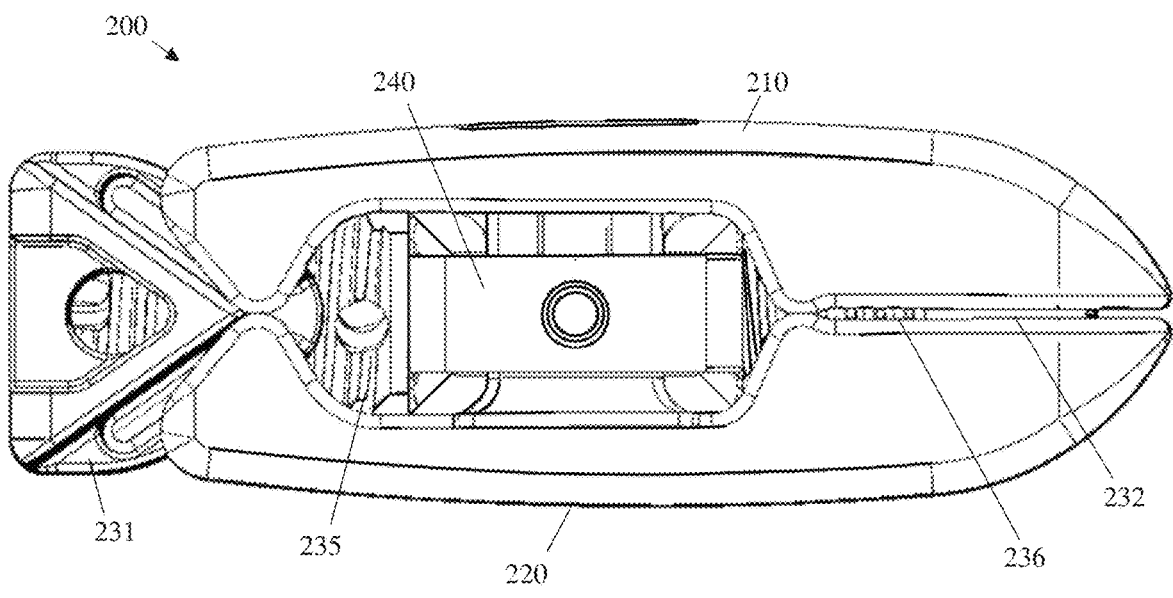
FIG. 11 shows a side view of the expandable spinal fusion implant in a first, collapsed configuration, in accordance with the embodiment of FIG. 10.

In FIG. 11, expandable spinal fusion implant 200 is shown in a collapsed configuration. The collapsed configuration provides a reduced profile and is particularly useful to aid in insertion of expandable spinal fusion implant 200 into an intervertebral disc space of a patient. A tapered distal end of the endplates 210, 220 is shown, which reduces an amount of force required to insert expandable spinal fusion implant 200 into a prepared intervertebral disc space of a patient.

Figure 12:
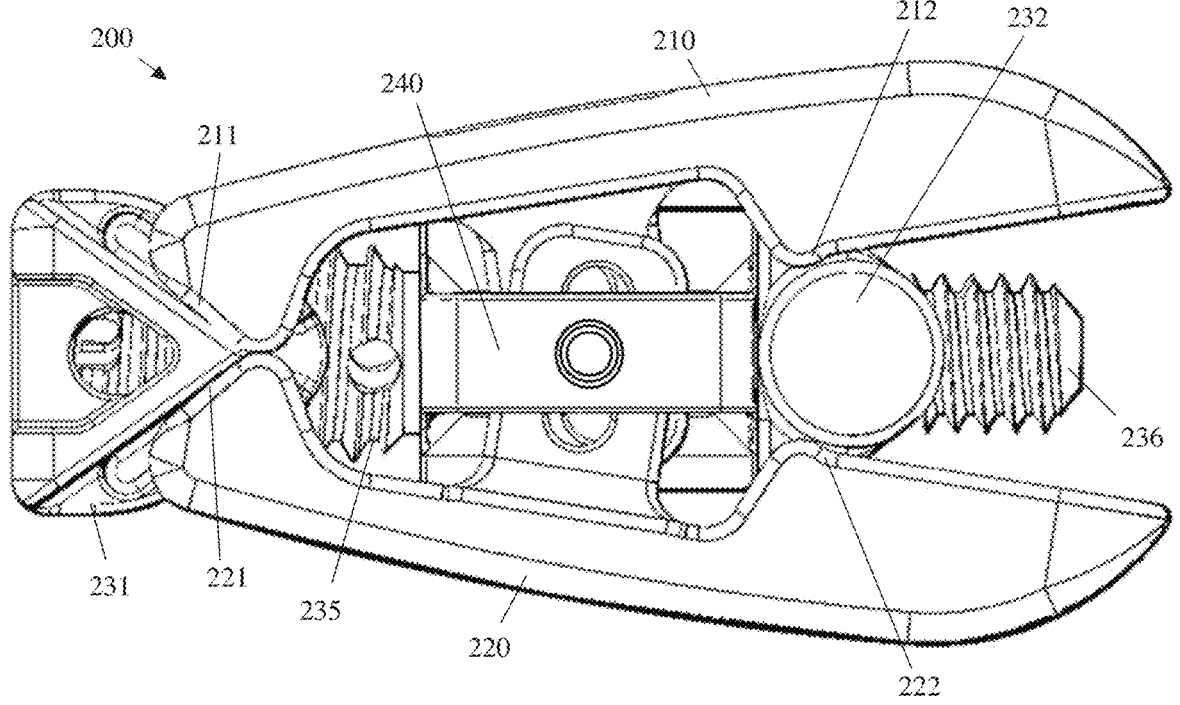
FIG. 12 shows a side view of the expandable spinal fusion implant adjusted to an exemplary angle of lordosis, in accordance with the embodiment of FIG. 10.

FIG. 12 shows expandable spinal fusion implant 200 in an expanded configuration. As one with skill in the art may appreciate, threaded barrel 232 is shown translated toward the center of expandable implant 200, with endplates 210, 220 shown pivoted to some angle of lordosis. Similar to the previous embodiment, if wedge 231 is translated toward the center of expandable spinal fusion implant 200 from this configuration, the ramps 211, 221 of first endplate 210 and second endplate 220 would travel up wedge 231, and the height of the expandable spinal fusion implant 200 would change. In fact, a near infinite number of heights and angles of lordosis may be achieved, hence only exemplary adjustments will be expressly shown. However, this should not be considered limiting as the full breadth of the range of motion of the endplates relative to the actuator has been contemplated and described herein.

Figure 13:
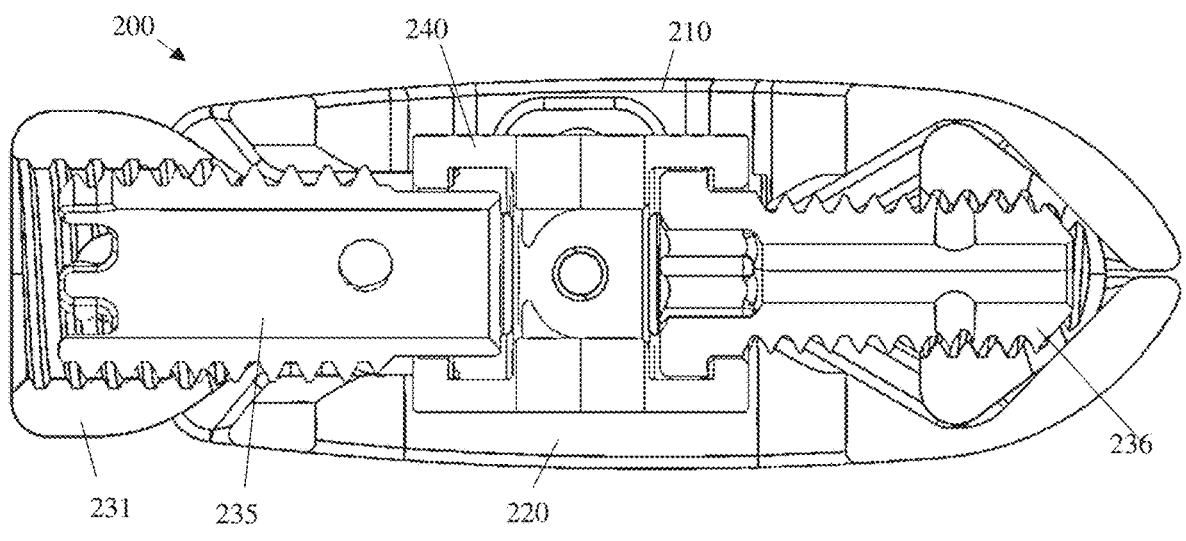
FIG. 13 shows a cross-sectional side view of the expandable spinal fusion implant in a first, collapsed configuration, in accordance with the embodiment of FIG. 10.
Figure 14:
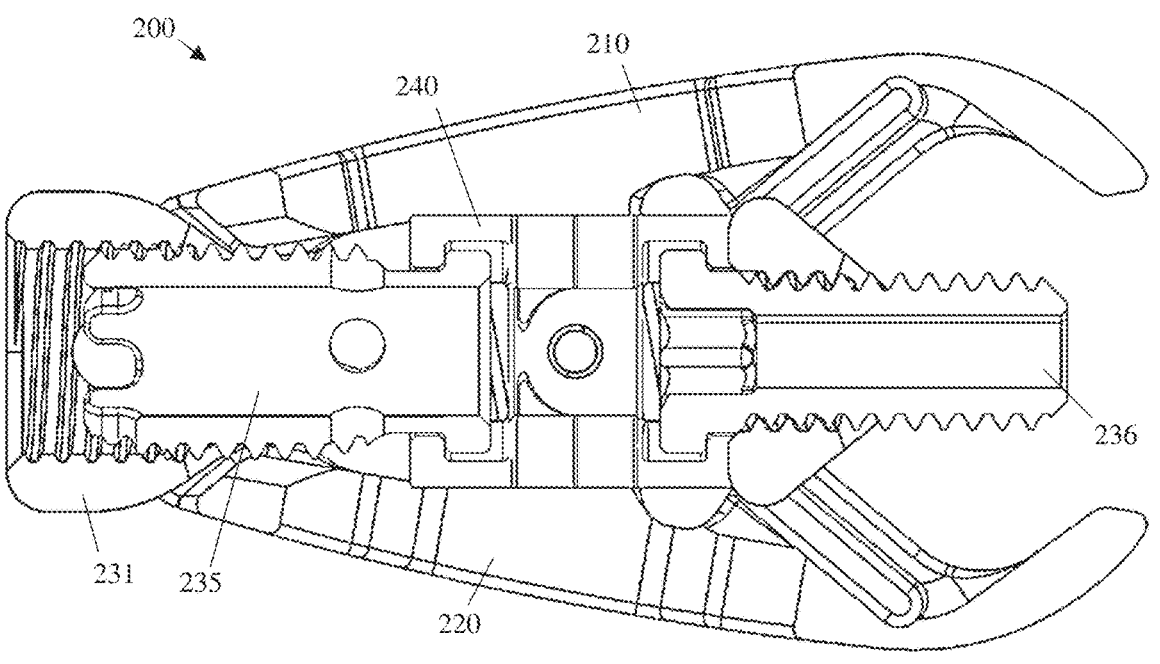
FIG. 14 shows a cross-sectional side view of the expandable spinal fusion implant adjusted to an exemplary angle of lordosis, in accordance with the embodiment of FIG. 10.

FIGS. 13-14 show cross-sectional views of the expandable spinal fusion implant 200 in a collapsed configuration and expanded configuration respectively. The expandable spinal fusion implant 200 includes: a first endplate 210 having a first barrel contact surface 212 and a first ramp 211, a second endplate 220 having a second barrel contact surface 222 and a second ramp 221, and a first lead screw 235 coupled to a second lead screw 236 by a coupler 240. First lead screw 235 may be configured to rotate independently of second lead screw 236. Threaded barrel 232 may be configured to translate along a length of second lead screw 236 as second lead screw 236 is rotated. Threaded barrel 232 may further be configured to communicate with first barrel contact surface 212 of first endplate 210 and second barrel contact surface 222 of second endplate 220 to displace first endplate 210 relative to second endplate 220 to change a dimension of expandable spinal fusion implant 200. Wedge 231 may be configured to translate along first lead screw 235 as first lead screw 235 is rotated, wedge 231 being configured to communicate with first ramp 211 of first endplate 210 and second ramp 221 of second endplate 220 to displace first endplate 210 relative to second endplate 220 to change a dimension of expandable spinal fusion implant 200.

Turning to FIGS. 15-17, expandable spinal fusion implant 200 with first endplate 210 and second endplate 220 is shown including tracks 218, 228. Tracks 218, 228 (FIGS. 15-16) may be configured to receive keyed elements 237 of threaded barrel 232 (FIGS. 15 and 17). Similarly, as shown in FIGS. 15-16, wedge 231 may include tracks 238 configured to receive keyed elements 217, 227 of first endplate 210 and second endplate 220, respectively. Communication between the tracks and keyed elements helps maintain a position of first endplate 210 relative to second endplate 220 as wedge 231 and threaded barrel 232 are translated along lead screws 235, 236.

FIG. 16 shows a linkage 213 of first endplate 210 and a linkage 223 of second endplate 220 which are coupled together by a pin 241 (FIG. 15) at coupler 240 to help moveably hold expandable spinal fusion implant 200 together. In the instant embodiment, first endplate 210 and second endplate 220 each have two linkages 213, 223.

FIG. 17 shows a threaded barrel 232, which includes a threaded aperture configured to receive at least a portion of a lead screw therethrough. Threaded barrel 232 includes a substantially circular endplate contact surface configured to communicate with the first barrel contact surface 212 of first endplate 210 and second barrel contact surface 222 of second endplate 220. The threaded barrel also includes a plurality of keyed elements 237. The keyed elements 237 are configured to communicate with tracks 218, 228 of first endplate 210 and second endplate 220.

Figure 18:
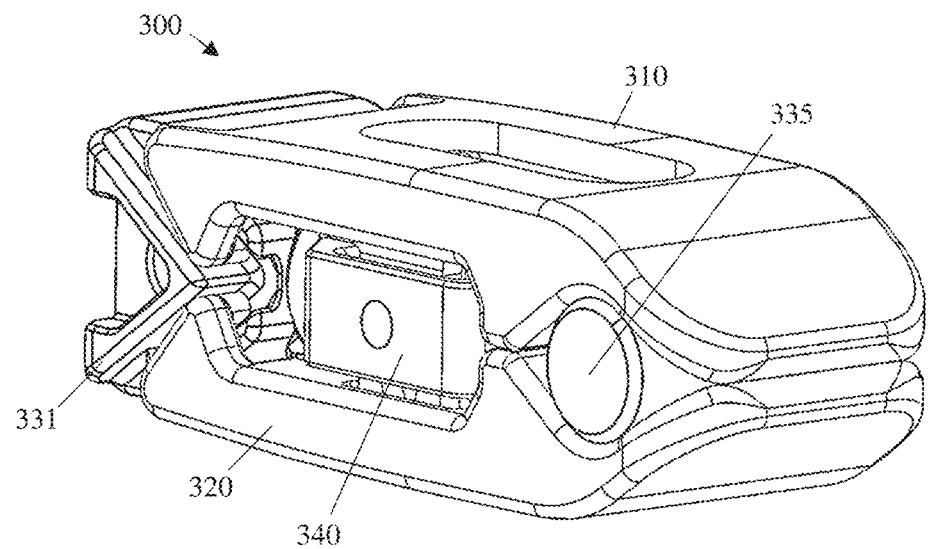
FIG. 18 shows a perspective view of an expandable spinal fusion implant in accordance with an embodiment of the disclosure.
Figure 19:
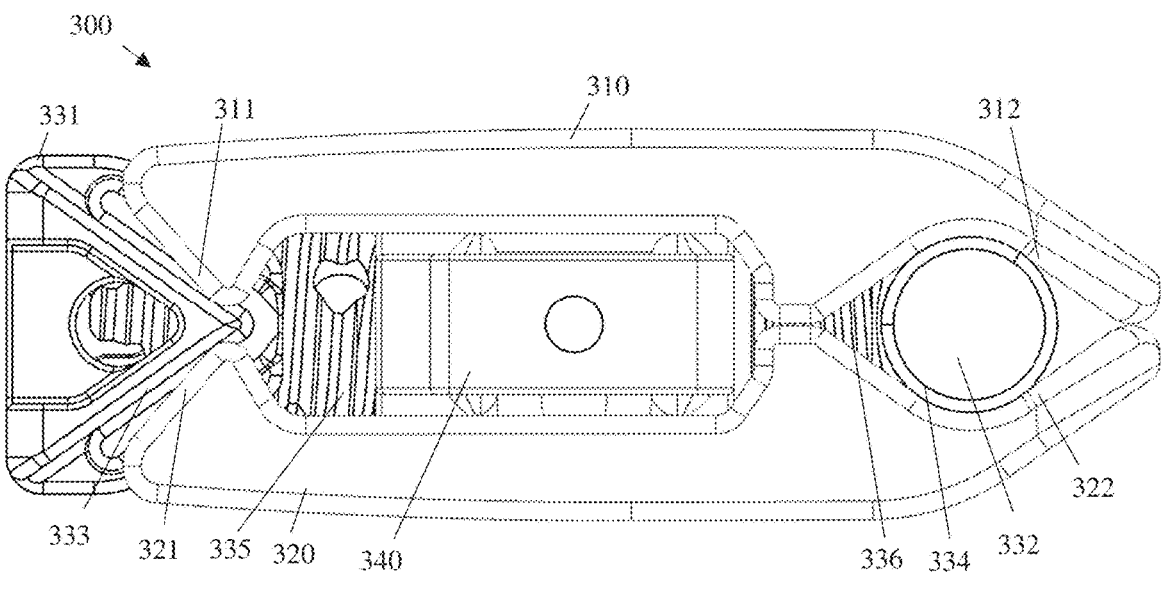
FIG. 19 shows a side view of the expandable spinal fusion implant in a first, collapsed configuration, in accordance with the embodiment of FIG. 18.
Figure 20:
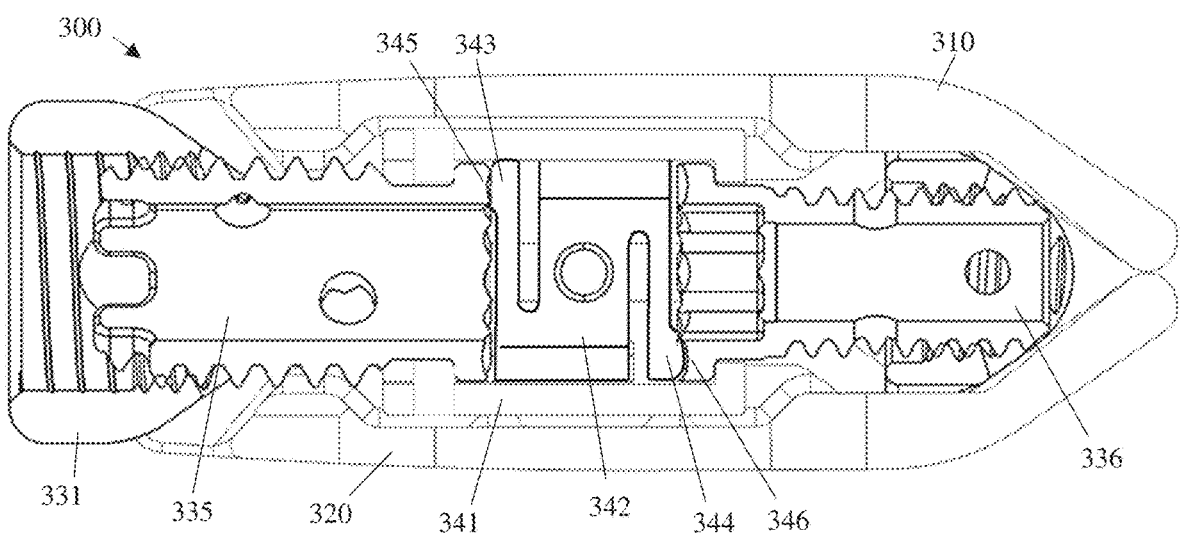
FIG. 20 shows a cross-sectional side view of the expandable spinal fusion implant in accordance with the embodiment of FIG. 18.

FIGS. 18-20 show an expandable spinal fusion implant 300 in accordance with a third embodiment. Expandable spinal fusion implant 300 includes: a first endplate 310 having a first barrel contact surface 312 and a first ramp 311, and a second endplate 320 having a second barrel contact surface 322 and a second ramp 321. A first lead screw 335 may be coupled to second lead screw 336 by a coupler 340, the first lead screw 335 being configured to rotate independently of second lead screw 336. Threaded barrel 332 may be configured to translate along a length of second lead screw 336 as second lead screw 336 is rotated. Barrel surface 334 of threaded barrel 332 may be configured to communicate with first barrel contact surface 312 of first endplate 310 and second barrel contact surface 322 of second endplate 320 to displace first endplate 310 relative to second endplate 320, thereby changing a dimension of expandable spinal fusion implant 300. Wedge 331 may be configured to translate along first lead screw 335 as first lead screw 335 is rotated. Wedge surface 333 of wedge 331 may be configured to communicate with first ramp 311 of first endplate 310 and second ramp 321 of second endplate 320 to displace first endplate 310 relative to second endplate 320 to change a dimension of expandable spinal fusion implant 300.

FIG. 20 shows a cross-sectional side view of expandable spinal fusion implant 300 including an anti-rotation mechanism. In this embodiment, coupler 340 includes an outer coupler 341 and a central spring piece 342. The central spring piece 342 includes a first spring biased element 343 configured to communicate with a plurality of indents 345 of first lead screw 235 and a second spring biased element 344 configured to communicate with a plurality of indents 346 of second lead screw 336. The first spring biased element 343 and the second spring biased element 344 are configured to prevent undesired rotation of the lead screws and prevent collapse of expandable spinal fusion implant 300. The central spring piece 342 may be annular and may further be configured to receive an instrument therethrough, for example the instrument configured to rotate second lead screw 336.

Figure 21:
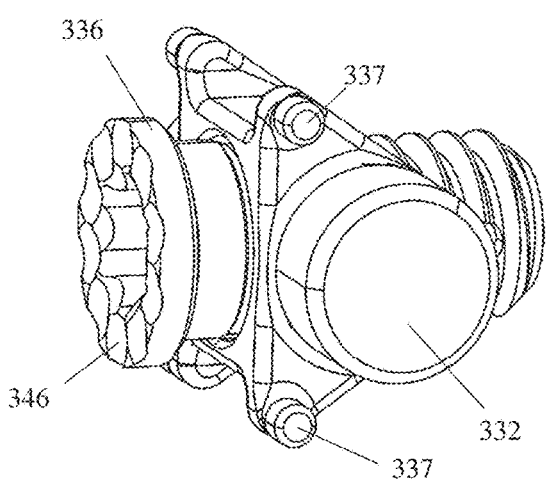
FIG. 21 shows a perspective view of a threaded barrel and a lead screw.

FIG. 21 shows a perspective view of second lead screw 336 in threaded engagement with threaded barrel 332. Threaded barrel 332 includes a plurality of keyed elements 337. Similar to previous embodiments, keyed elements 337 are configured to communicate with tracks of first endplate 310 and second endplate 320, e.g., similar to tracks 218, 228 as shown in FIGS. 15-16. Communication between the tracks and keyed elements helps maintain a position of first endplate 310 relative to second endplate 320 as wedge 331 and threaded barrel 332 are translated along lead screws 335, 336. Second lead screw 336 is also shown including a plurality of indents 346 configured to communicate with the second spring biased element 344 of the central spring piece 342.

Threaded barrel 332 includes a substantially circular endplate contact surface configured to communicate with first barrel contact surface 312 of first endplate 310 and second barrel contact surface 322 of second endplate 320, to displace first endplate 310 relative to second endplate 320 to change a dimension of expandable spinal fusion implant 300.

Figure 22:
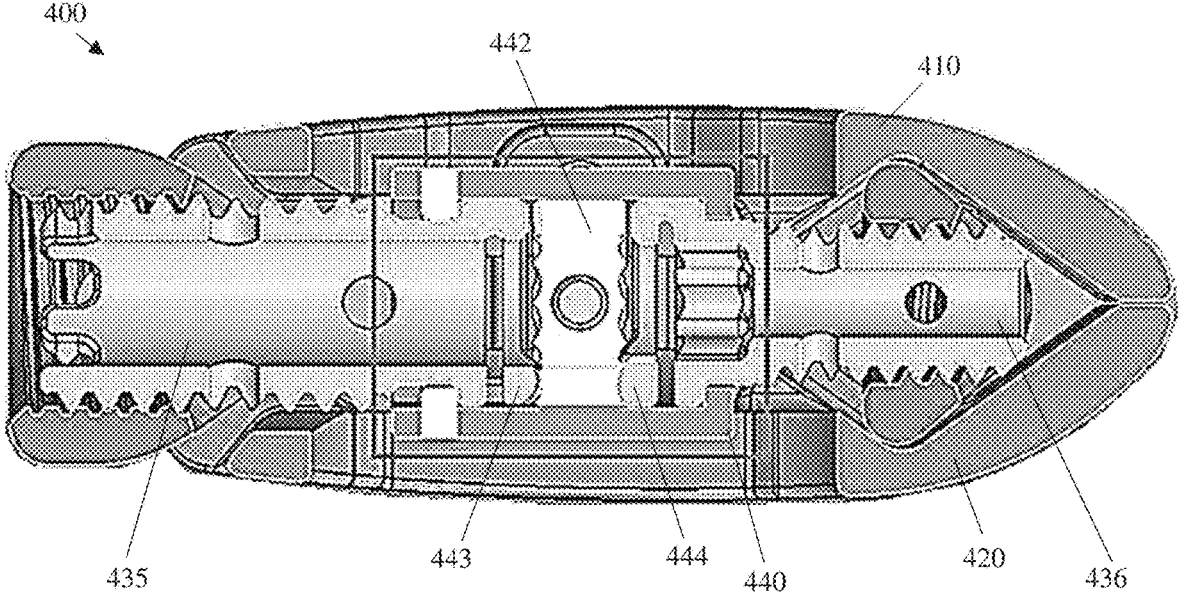
FIG. 22 shows a cross-sectional side view of an expandable spinal fusion implant in accordance with an embodiment of the disclosure.
Figure 23:
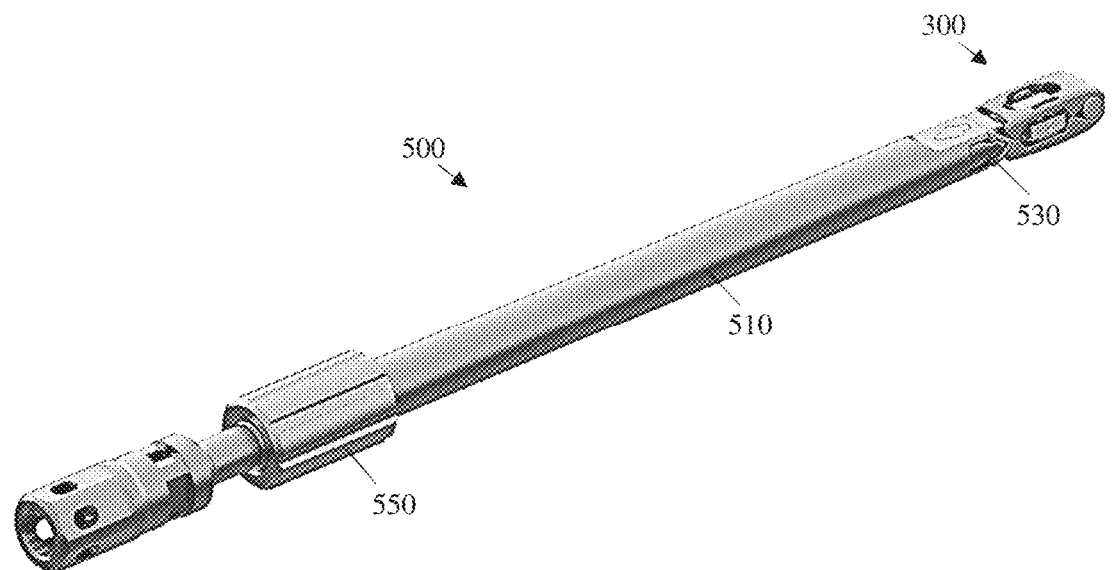
FIG. 23 shows a perspective view of an inserter in accordance with an embodiment having an expandable spinal fusion implant removably secured to a tip thereof.

FIG. 22 shows a cross sectional view of an expandable spinal fusion implant 400 having a first endplate 410, a second endplate 420, and a coupler 440 in accordance with a fourth embodiment. The embodiment of FIG. 22 is similar to the previous embodiments except that the spring biased elements of the antirotation mechanism may be built into the lead screws 435, 436. For example, first lead screw 435 includes a first spring biased element 443, and second lead screw 436 includes second spring biased element 444. First spring biased element 443 and second spring biased element 444 are configured to communicate with central coupler 442. Central coupler 442 includes a plurality of divots configured to communicate with the lead screws, to prevent an undesired rotation of the lead screws.

FIGS. 45-52 show an expandable spinal fusion implant 800 in accordance with a fifth embodiment. As shown, the expandable spinal fusion implant 800 is shown including: a first endplate 810 (FIGS. 45-46 and 49-51) having a first barrel contact surface 812 (FIGS. 45-46, 49, and 50), a second endplate 820 (FIGS. 45-49 and 51-52) having a second barrel contact surface 822 (FIGS. 45-49 and 51-52), a first lead screw 835 (FIGS. 51-52) having a length and a wedge 831 configured to translate along the length of the first lead screw 835 as the first lead screw 835 is rotated, and a second lead screw 836 having a length and a threaded barrel 832 configured to translate along the length of the second lead screw 836 as second lead screw 836 is rotated. A surface of threaded barrel 832 is configured to communicate with first barrel contact surface 812 of first endplate 810 and second barrel contact surface 822 of second endplate 820 to move first endplate 810 relative to second endplate 820 and change a dimension of expandable spinal fusion implant 800.

In the illustrated embodiment, first lead screw 835 is movable independently of and/or simultaneously with second lead screw 836, with first lead screw 835 and second lead screw 836 being configured to be rotated independently. Lead screws 835, 836 can be cannulated such that bone graft can be positioned therein. At least a portion of actuator 830 is disposed between first endplate 810 and second endplate 820.

Threaded barrel 832 is configured to translate along the length of second lead screw 836 as second lead screw 836 is rotated, and wedge 831 is configured to translate along the length of first lead screw 835 as first lead screw 835 is rotated.

Threaded barrel 832 includes a substantially circular endplate contact surface 834 (FIG. 49) configured to communicate with first barrel contact surface 812 of first endplate 810 and second barrel contact surface 822 of second endplate 820 as threaded barrel 832 is translated along the length of second lead screw 836.

Wedge 831 is configured to translate along the length of first lead screw 835 as first lead screw 835 is rotated. First endplate 810 includes a first ramp 811 configured to communicate with wedge 831 and second endplate 820 includes a second ramp 821 configured to communicate with wedge 831.

First endplate 810 and second endplate 820 include grooves 813, 823 (FIGS. 45-48 and 52) configured to communicate with bosses 842 positioned on opposing sides of coupler 840 to moveably secure first endplate 810 relative to second endplate 820. As first endplate 810 and second endplate 810 move, the bosses 842 ride within grooves 813, 823 to ensure that endplates 810, 820 expand in a symmetric fashion. The dimension of the expandable spinal fusion implant 800 to be changed may include, e.g., a height and/or an angle between first endplate 810 and second endplate 820.

Figure 45:
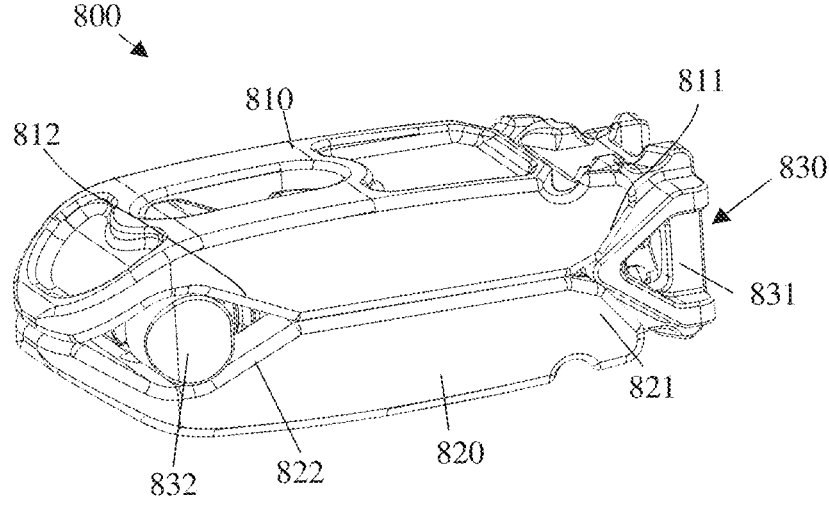
FIG. 45 shows a perspective view of an expandable spinal fusion implant in a collapsed configuration according to another embodiment of the disclosure.
Figure 47:
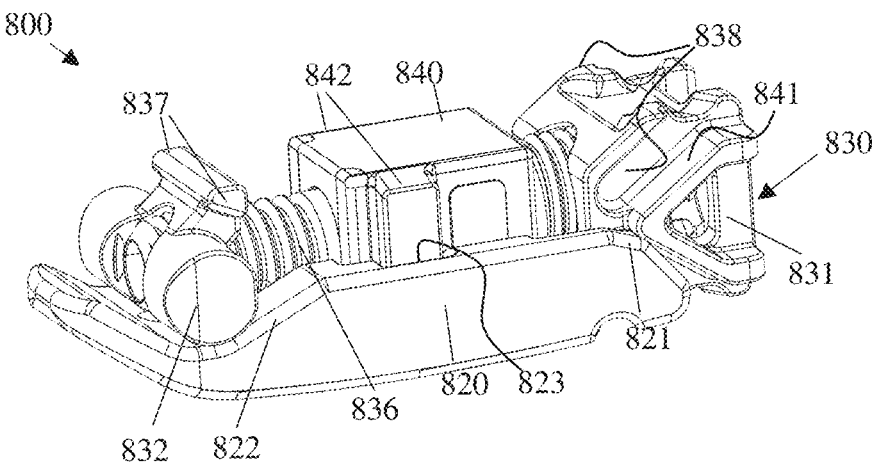
FIG. 47 shows a perspective view of the expandable spinal fusion implant of FIG. 45 with the first end plate removed.

In FIGS. 45 and 47, expandable spinal fusion implant 800 is shown in a collapsed configuration. The collapsed configuration provides a reduced profile and is particularly useful to aid in insertion of expandable spinal fusion implant 800 into an intervertebral disc space of a patient. A tapered distal end of endplates 810, 820 is shown, which reduces an amount of force required to insert expandable spinal fusion implant 800 into a prepared intervertebral disc space of a patient.

Figure 46:
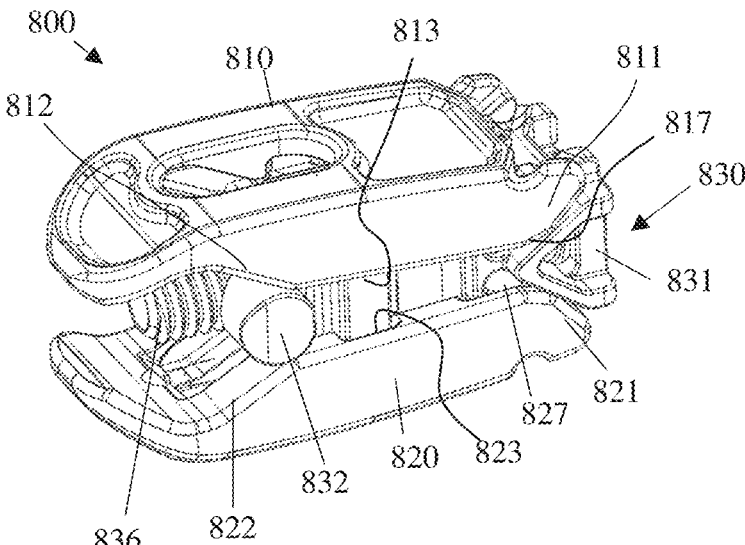
FIG. 46 shows a perspective view of the expandable spinal fusion implant of FIG. 45 in one example of an expanded configuration.
Figure 48:
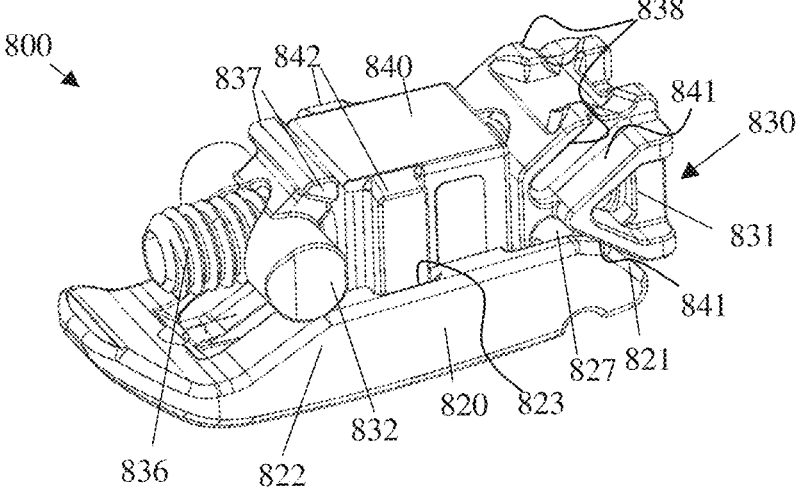
FIG. 48 shows a perspective view of the expandable spinal fusion implant of FIG. 46 with the first end plate removed.

FIGS. 46 and 48 show expandable spinal fusion implant 800 in one example of an expanded configuration. As one with skill in the art may appreciate, threaded barrel 832 is shown translated toward the center of the expandable implant 800, with the endplates 810, 820 shown pivoted to some angle of lordosis. Similar to the previous embodiments, upon translation of wedge 831 toward the center of expandable spinal fusion implant 800 from this configuration, ramps 811, 821 of first endplate 810 and second endplate 820 would travel up wedge 831, and the height of expandable spinal fusion implant 800 would change. A near infinite number of heights, angles of lordosis, and combinations thereof may be achieved, hence only exemplary adjustments will be expressly shown. However, this should not be considered limiting as the full breadth of the range of motion of the endplates relative to the actuator has been contemplated and described herein.

Figure 49:
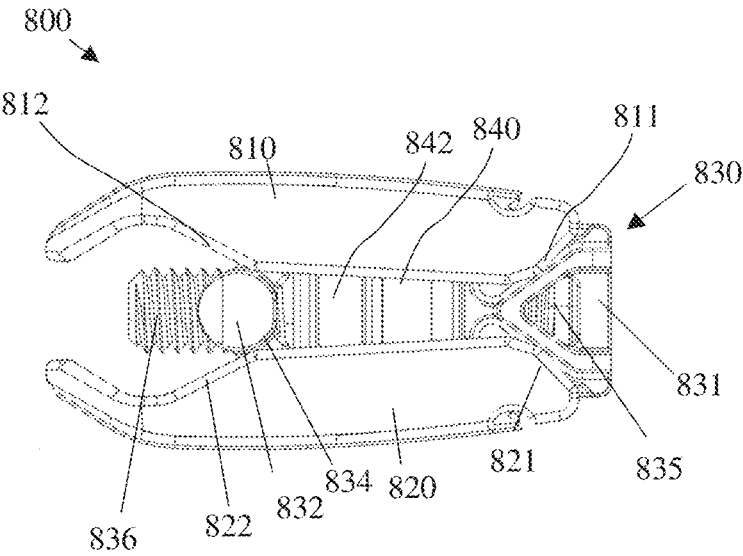
FIG. 49 shows a side view of the expandable spinal fusion implant in the expanded configuration of FIG. 46.
Figure 50:
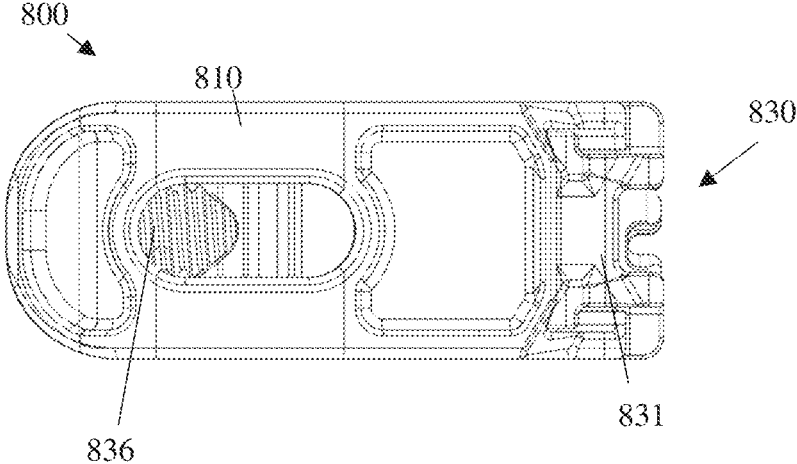
FIG. 50 shows a top view of the expandable spinal fusion implant in the expanded configuration of FIG. 46.
Figure 51:
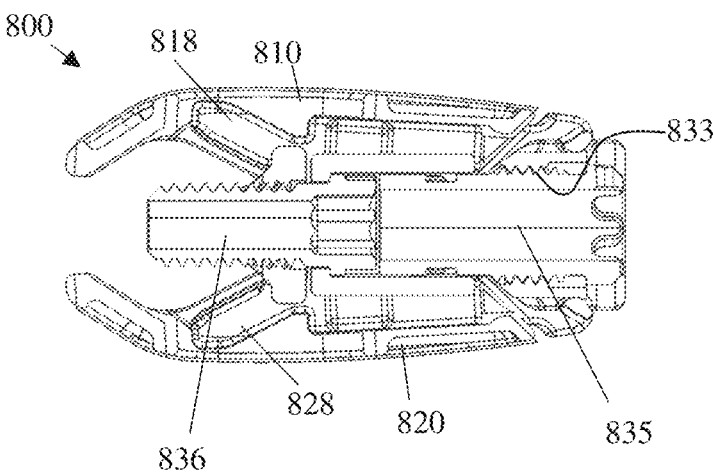
FIG. 51 shows a cross-sectional view of the expandable spinal fusion implant of FIG. 49.
Figure 52:
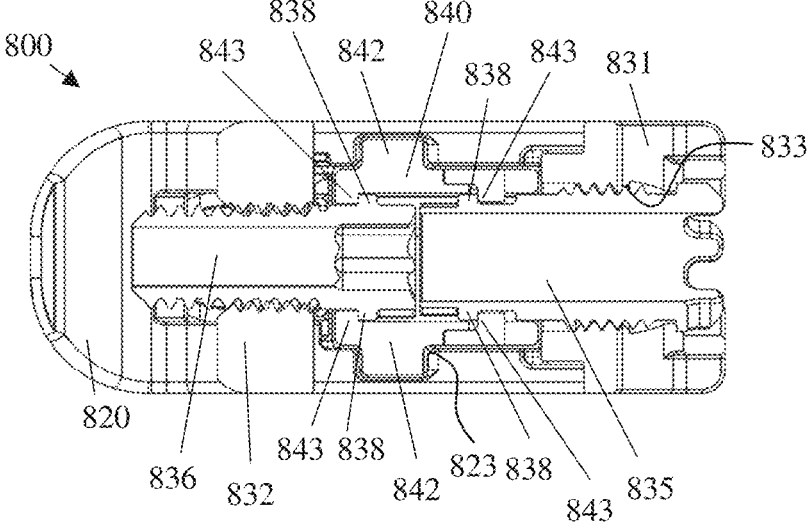
FIG. 52 shows a cross-sectional view of the expandable spinal fusion implant of FIG. 40.

FIGS. 49 and 51 show a side view of the expandable spinal fusion implant 800 in an expanded configuration, with FIG. 51 showing a cross-sectional side view. FIGS. 50 and 52 show a top view of the expandable spinal fusion implant 800 in an expanded configuration, with FIG. 52 showing a cross-sectional top view. The expandable spinal fusion implant 800 includes: a first endplate 810 having a first barrel contact surface 812 and a first ramp 811, a second endplate 820 having a second barrel contact surface 822 and a second ramp 821. A first lead screw 835 may be coupled to a second lead screw 836 by a coupler 840, the first lead screw 835 configured to rotate independently of second lead screw 836. A threaded barrel 832 may be configured to translate along a length of second lead screw 836 as second lead screw 836 is rotated, threaded barrel 832 being configured to communicate with first barrel contact surface 812 of first endplate 810 and second barrel contact surface 822 of second endplate 820, to displace first endplate 810 relative to second endplate 820 to change a dimension of the expandable spinal fusion implant 800. Wedge 831 may be configured to translate along first lead screw 835 as first lead screw 835 is rotated, wedge 831 may further be configured to communicate with first ramp 811 of first endplate 810 and second ramp 821 of second endplate 820 to displace first endplate 810 relative to second endplate 820 to change the dimension of expandable spinal fusion implant 800.

Turning to FIG. 51, a cross-sectional view of expandable spinal fusion implant 800 with first endplate 810 and second endplate 820 are shown including tracks 818, 828, configured to receive keyed elements 837 (FIG. 53-54) of threaded barrel 832. Similarly, wedge 831 is shown including tracks 838 (FIGS. 48 and 54) configured to receive keyed elements 817, 827 (FIGS. 46 and 48) of first endplate 810 and second endplate 820. Communication between the tracks and keyed elements helps maintain a position of first endplate 810 relative to second endplate 820 as wedge 831 and threaded barrel 832 translate along lead screws 835, 836. In addition, communication between the tracks and keyed elements prevent endplates 810, 820 from separating or lifting off of threaded barrel 832 or wedge 831, respectively. In addition, such a configuration forces endplates 810, 820 closed when collapsing expandable spinal fusion device 800.

Figure 53:
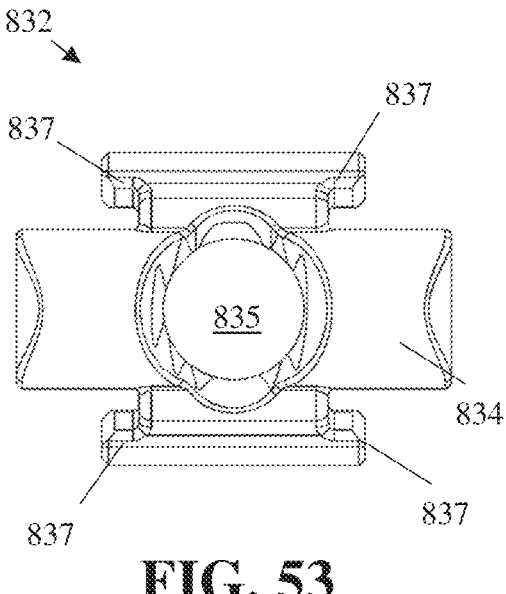
FIG. 53 shows a front view of a threaded barrel according to embodiments of the disclosure.

FIG. 53 shows a threaded barrel 832. Threaded barrel 832 includes a threaded aperture 835 configured to receive at least a portion of a lead screw, e.g., lead screw 836, therethrough. Threaded barrel 832 includes a substantially circular endplate contact surface 834 configured to communicate with first barrel contact surface 812 of first endplate 810 and second barrel contact surface 822 of second endplate 820. Threaded barrel 832 also includes a plurality of keyed elements 837. Keyed elements 837 are configured to communicate with tracks 818, 828 of first endplate 810 and second endplate 820.

Wedge 831 includes a threaded aperture 833 (FIGS. 51-52) configured to receive at least a portion of a lead screw, e.g., lead screw 835, therethrough. Wedge 831 includes wedge surfaces 841 (FIGS. 48 and 55) configured to communicate with the first ramp 811 of the first end plate 810 and second ramp 821 of second endplate 820. Wedge 831 also includes tracks 838 configured to receive keyed elements 817, 827 of first endplate 810 and second endplate 820.

As shown in FIG. 52, coupler 840 includes abutments or stops 843 therein for abutting against abutments or stops 838 on each lead screw 835, 836. As a result, coupler 840 secures lead screws 835, 836 in position axially relative to each other while allowing independent rotation of lead screws 835, 836 relative to each other. In addition, lead screws 835, 836 are prevented from separating from coupler 840.

Figure 54:
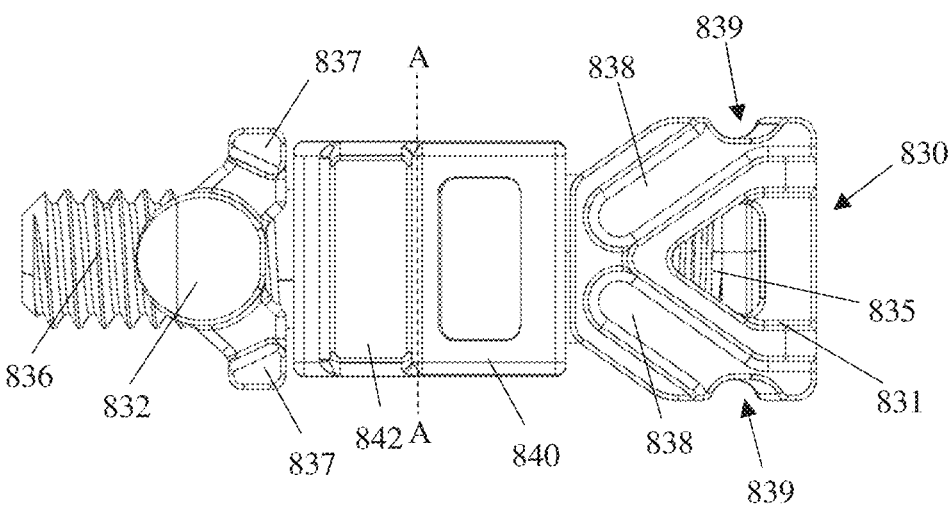
FIG. 54 shows a side view of the actuator of the expandable spinal fusion implant according to the embodiment shown in FIG. 49 with the first and second endplates removed.

FIG. 54 shows an enlarged side view of actuator 830 with endplates 810, 820 removed for clarity. As shown, wedge 831 also shows scalloped portions 839 to help identify the wedge 831 versus instruments associated with the expandable spinal fusion implant 800, e.g., an inserter or expansion driver.

Figures 55, 56:
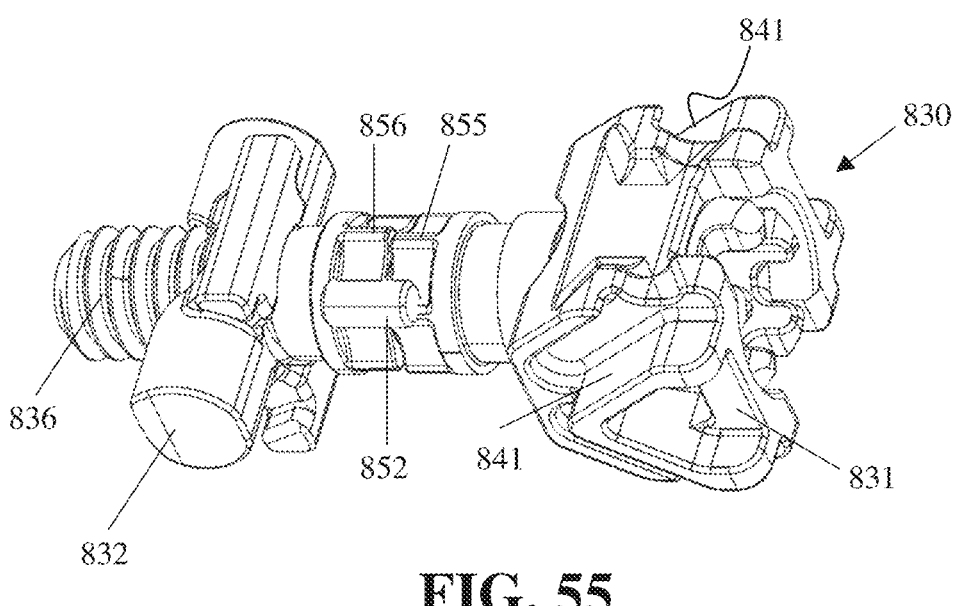
FIG. 55 shows a perspective view of the actuator of the expandable spinal fusion implant according to the embodiment shown in FIG. 49 with the coupler and first and second plates removed.
FIG. 56 shows a cross-sectional view of the coupler having the lead screws positioned therein taken along line A-A of FIG. 54.

FIG. 55 shows an enlarged perspective view of actuator 830 with coupler 840 and endplates 810, 820 removed for clarity. FIG. 56 shows a sectional view taken through line A-A of FIG. 54. As shown, at least one pin 852 is positioned about heads 855, 856 of lead screws 835, 836. Pin 852 provides a passive locking mechanism to prevent lead screws 835, 836 from unintentionally rotating or adjusting the implant height. Specifically, pin 852 sits within groove 854 between ridges on heads 855, 856 of lead screws 835, 836 when actuator 830 is not being actuated. During actuation, however, pin 852 is configured to deform to enable rotation of lead screws 835, 836 due to the force supplied by the expansion instrument, e.g., an expansion driver. As shown, coupler 840 includes at least one complementary groove 854 for housing at least one pin 852 therein.

To aid in the fusion process, it may be desirable to pack expandable spinal fusion implant 800 with bone graft or bone graft substitute material. As one with skill in the art may appreciate, in the various embodiments presented herein, as the wedges and threaded barrels are translated away from the center of the expandable spinal fusion implant to expand the expandable spinal fusion implant, a void is created in the central volume. Expandable spinal fusion implant 800 may be prepacked with bone graft or bone graft substitute material or packed in situ, when expandable spinal fusion implant 800 is placed and expanded within the intervertebral space of the patient. First and second endplates 810, 820 include fusion apertures configured allow communication between the vertebral bodies and any bone graft or bone graft substitute material provided to the inner void. The bone graft or bone graft substitute material may be provided through the hollow first lead screw or through a separate aperture. As shown and described herein, first and second endplates 810, 820 are intended to communicate with the adjacent vertebral bodies when the implant 800 is inserted into the intervertebral space of a patient. As such, endplates 810, 820 may further include anti-migration features configured to restrict slippage in the disc space and porous features configured to aid in the fusion process.

Turning to FIGS. 23-44 and 57-71 generally, instruments for use in connection with an expandable spinal fusion implant 100, 200, 300, 400, 800 are provided. Many embodiments are described with respect to expandable spinal fusion implant 300 for purposes of brevity. However, each instrument may be equally useful in connection with expandable spinal fusion implants 100, 200, 400, 800.

According to one embodiment, a surgical instrument may include: an inserter, an expansion driver and an indicator handle. The inserter may be cannulated and may be configured to telescopically receive the expansion driver. The inserter may include a plurality of hooks configured to removably attach an expandable spinal fusion device to the inserter with the plurality of hooks are configured to be splayed open and closed.

The expansion driver may include an outer driver and an inner driver, with the outer driver disposed annularly around the inner driver. The expansion driver may be configured to extend through the cannulated inserter with the outer driver configured to communicate with a first lead screw of the expandable spinal fusion implant and the inner driver configured to communicate with a second lead screw of the expandable spinal fusion implant. The expansion driver may include a clutch mechanism, the clutch mechanism may be configured to selectively engage the outer driver and the inner driver. The clutch mechanism may include a first face clutch and a second face clutch, the first face clutch configured to selectively engage a first clutch member and a second face clutch configured to selectively engage a second clutch member. Upon a selective engagement of the first face clutch and the first clutch member, a rotation of the first face clutch is communicated to the first clutch member, the first clutch member communicating the rotation to the outer driver, and the outer driver communicating the rotation to the first lead screw of the expandable spinal fusion implant. Upon a selective engagement of the second face clutch and the second clutch member, a rotation of the second face clutch is communicated to the second clutch member, the second clutch member communicating the rotation to the inner driver, and the inner driver communicating the rotation to the second lead screw of the expandable spinal fusion implant. In some embodiments, the inner driver is configured to extend through a hollow cavity of the first lead screw to communicate with the second lead screw. Rotation of both lead screws upon rotation of the inner driver is prevented by communication of the first lead screw with the outer driver.

The indicator handle may be configured to be removably secured to the inserter. The indicator handle may be configured to receive at least a portion of the expansion driver. The indicator handle may include an indicator display configured to communicate an amount of adjustment of an expandable spinal fusion device. The indicator handle may include a scale configured to measure an amount of adjustment of the expandable spinal fusion device. The indicator handle may include a first indicator display and a second indicator display. The indicator handle may include a first scale and a second scale. The first scale may be configured to measure an amount of posterior adjustment of the expandable spinal fusion implant and the second scale may be configured to measure an angle of lordosis of the expandable spinal fusion device. The first indicator display may be configured to communicate an amount of posterior adjustment of the expandable spinal fusion implant and the second indicator display may be configured to communicate an angle of lordosis of the expandable spinal fusion device. The first scale may include a moving scale configured to move upon a rotation of a first clutch member of the expansion driver. The second scale may include a moving scale configured to move upon a rotation of a second clutch member of the expansion driver.

FIGS. 23-27 show an inserter 500 in accordance with a first embodiment. The inserter 500 may be used to place expandable spinal fusion implants, e.g., implants 100, 200, 300, 400, 800 into the intervertebral disc space of a patient during surgery. The inserter 500 includes an outer shaft 510, an inner shaft 520, two arms 530 and two buttons 540.

Figure 24:
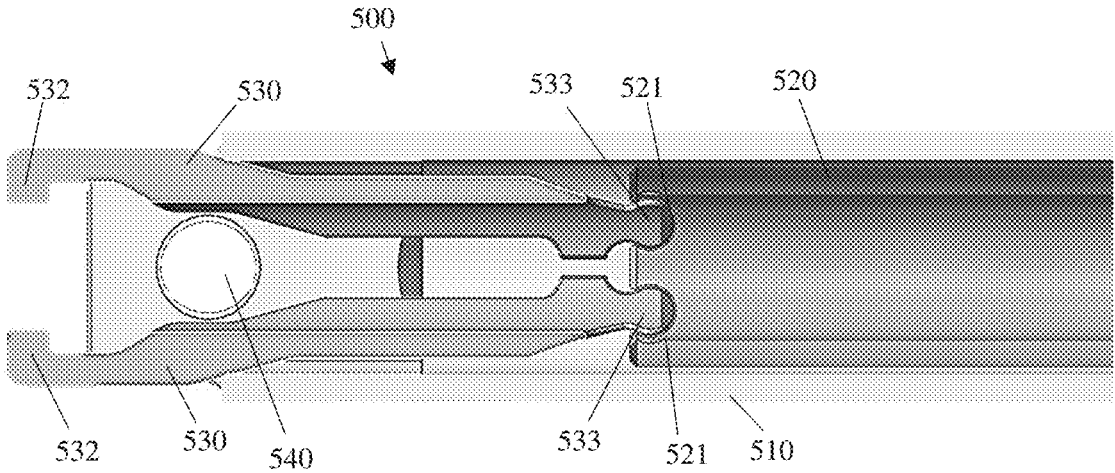
FIG. 24 shows a cross-sectional side view of the tip of the inserter.

Inserter 500 may be removably secured to an expandable spinal fusion implant 300 (FIG. 23) by the two arms 530 of the inserter 500. The arms 530 can be splayed open when the outer shaft 510 is drawn back in a proximal direction. Buttons 540 disposed on outer shaft 510 engage the ramps on the inside of arms 530. Arms 530 may be urged closed when outer shaft 510 is pushed forward in a distal direction, clamping arms 530 together. Arms 530 have cylindrical teeth 532 disposed on a distal end of each arm 530 (FIG. 24). Teeth 532 fit into and removeably secure the inserter 500 to inserter apertures of the expandable spinal fusion implant 300. Arms 530 allow inserter 500 to remain cannulated for instrumentation to be passed through the cannula. Inserter 500 has proximal features which allow for attachment of additional instruments for example: a counter torque handle, a removable indicator handle 700, and a navigation array.

Thumbwheel 550 is configured such that rotation thereof actuates movement of outer shaft 510 relative to inner shaft 520. Inner shaft 520 has a plurality of apertures 521 at the tip. These apertures 521 are configured to receive a keyed portion 533 of each of the two arms 530. When outer shaft 510 is drawn back, keyed portions 533 of arms 530 are configured to pivot about a point within inner shaft 520, thereby eliminating the need for pins to secure the arms to inner shaft 520.

Figure 25:
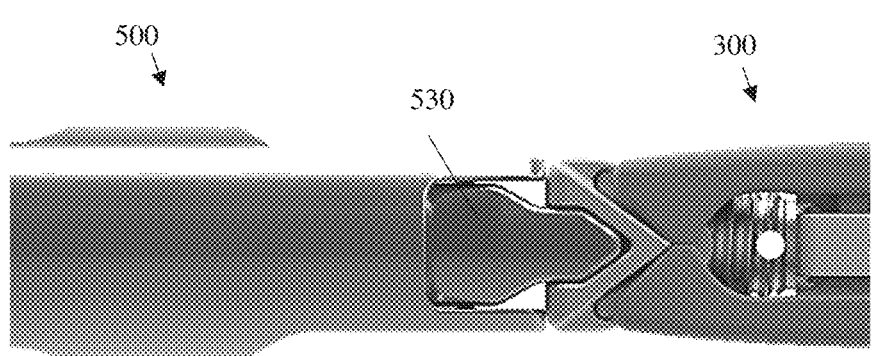
FIG. 25 shows a side view of the tip of the inserter having an expandable spinal fusion implant removably secured thereto.

FIG. 25 shows a side view of the inserter 500, with arms 530 of inserter 500 removably secured to expandable spinal fusion implant 300. In this embodiment of expandable spinal fusion implant 300, wedge 331 has two apertures configured to receive the cylindrical teeth 532 of inserter 500.

Figure 26:
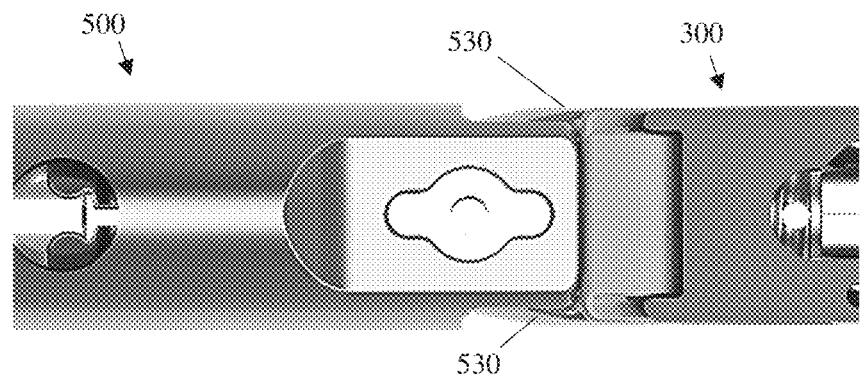
FIG. 26 shows a top view of the tip of the inserter having the expandable spinal fusion implant removably secured to thereto.
Figure 27:
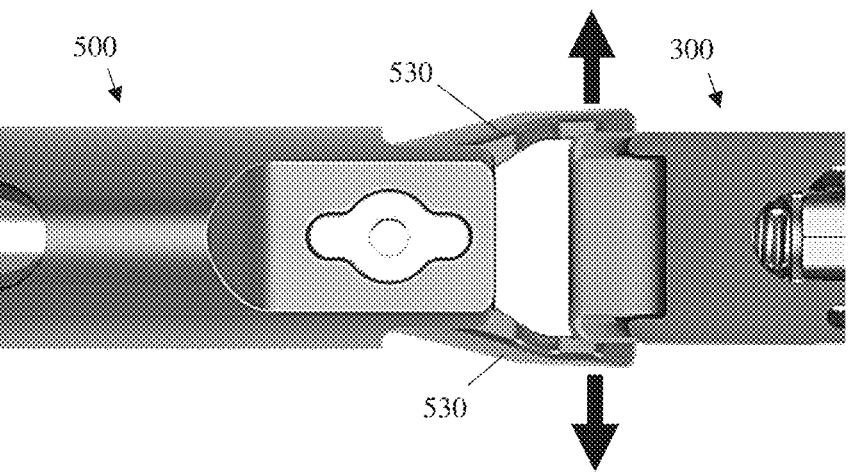
FIG. 27 shows a top view of the tip of the inserter with the arms of the inserter splayed open, and the inserter being removed from the expandable spinal fusion implant.

FIG. 26 shows a top view of the inserter 500, with arms 530 of inserter 500 removably secured to expandable spinal fusion implant 300. As one with skill in the art can appreciate, and as is described above, pulling outer shaft 510 of inserter 500 in a proximal direction will cause arms 530 of the inserter 500 to open. FIG. 27 shows inserter 500 with arms 530 splayed open and configured to be removed from expandable spinal fusion implant 300. Note that the motion of arms 530 when outer shaft 510 is retracted is shown by the provided bold arrows.

This functionality allows a surgeon to removably secure expandable spinal fusion implant 300 to inserter 500, deliver expandable spinal fusion implant 300 to the intervertebral disc space of the patient, and remove inserter 500 from expandable spinal fusion implant 300 while utilizing minimal access techniques.

Figure 28:
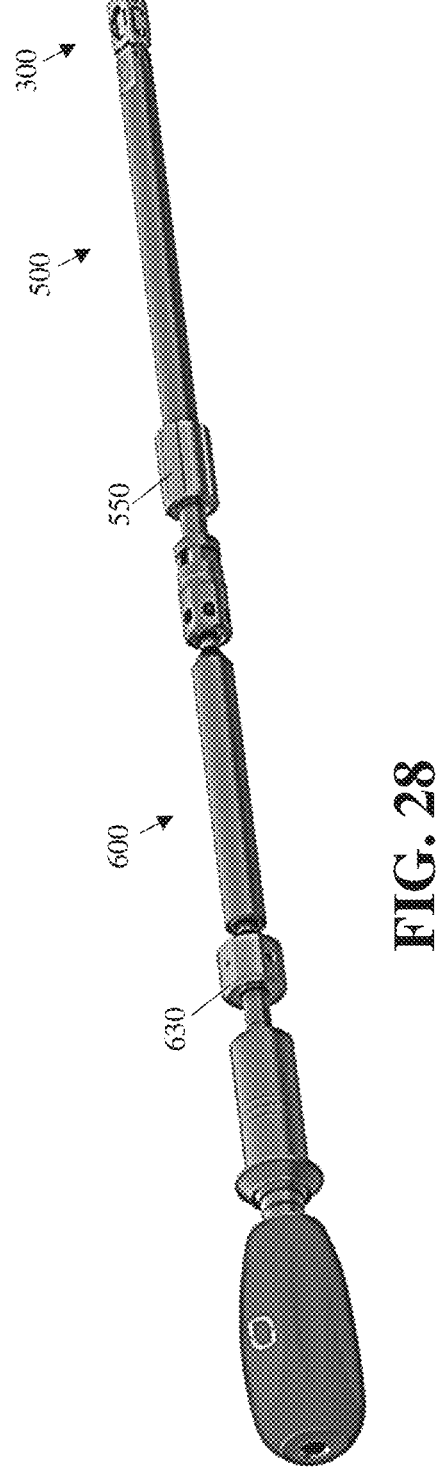
FIG. 28 shows an expansion mechanism removably attached to an inserter having an expandable spinal fusion implant removably secured to a tip thereof, in accordance with an embodiment of the disclosure.

FIG. 28 shows an expansion driver 600 in accordance with a first embodiment. At least a portion of expansion driver 600 is configured to pass through a hollow cavity of inserter 500 and engage with first lead screw 335 and second lead screw 336 of expandable spinal fusion implant 300 (FIGS. 18-20).

Figures 29, 30:
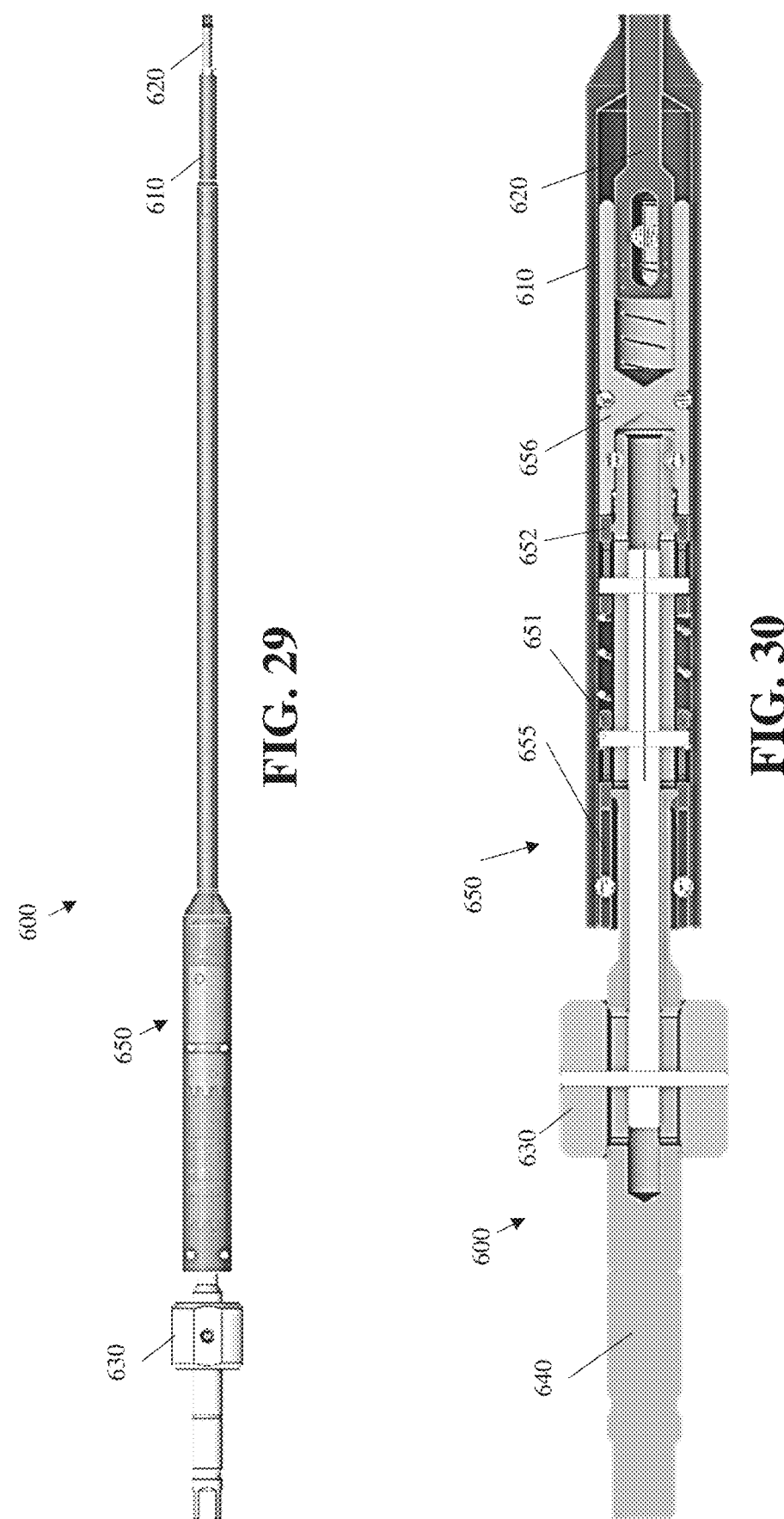
FIG. 29 shows a side view of the expansion driver in accordance with the embodiment of FIG. 28.
FIG. 30 shows an enhanced cross-sectional side view of the expansion driver.

As shown in FIGS. 29-30, expansion driver 600 includes an inner driver 620, an outer driver 610, and a clutch 650. In this embodiment, inner driver 620 is a hexalobe driver and outer driver 610 is a crown driver. Inner driver 620 is configured to expand the anterior portion of expandable spinal fusion implant 300 by rotating second lead screw 336, which is configured to move first endplate 310 relative to second endplate 320 as described above. Outer driver 610 is configured to expand the posterior portion of expandable spinal fusion implant 300 by rotating first lead screw 335, which is configured to move first endplate 310 relative to second endplate 320 as described above. When inner driver 620 and outer driver 610 are actuated together, expandable spinal fusion implant 300 expands in height. When inner driver 620 and outer driver 610 are actuated separately, an angle of lordosis is adjusted.

Inserter 500 and expansion driver 600 provide a full range of adjustment of expandable spinal fusion implant 300 with a single, easy to use instrument that can be used to perform multiple functions without being removed to switch between expansion modes. Expansion driver 600 has an adjustment knob 630 that allows the surgeon to selected a desired aspect of expandable spinal fusion implant 300 to be actively expanded, e.g., anterior, posterior, or both anterior and posterior.

Turning to FIG. 30, when a surgeon wants to expand either or both of the anterior portion and posterior portion of the expandable spinal fusion device, the surgeon or user may rotate the adjustment knob 630 to activate clutch 650. Clutch 650 includes a first face clutch 651, a second face clutch 652, a first clutch 655, and a second clutch 656. First face clutch 651 is configured to selectively engage first clutch 655, with first clutch 655 configured to communicate with and rotate outer driver 610. Outer driver 610 is configured to communicate rotation to first lead screw 335 of expandable spinal fusion implant 300. Second face clutch 652 is configured to selectively engage second clutch 656, with second clutch 656 configured to rotate inner driver 620, which in turn is configured to communicate rotation to second lead screw 336 of expandable spinal fusion implant 300.

If a surgeon wants to expand both the anterior portion and the posterior portion of expandable spinal fusion implant 300 simultaneously, rotation of adjustment knob 630 activates clutch 650, which allows first face clutch 651 to engage first clutch 655, and second face clutch 652 to engage second clutch 656. Thus, upon a rotation of input shaft 640, torque is transmitted to first face clutch 651 and second face clutch 652, and in turn transmitted to first clutch 655 and second clutch 656. First clutch 655 is directly connected to outer driver 610, and second clutch 656 is directly connected to inner driver 620. Therefore, rotation of input shaft 640 will result in actuation of both the anterior portion and the posterior portion of expandable spinal fusion implant 300.

To selectively adjust either the anterior portion or the posterior portion of expandable spinal fusion implant 300, the surgeon may actuate adjustment knob 630 to select a particular mode of adjustment for selective expansion of the anterior portion or the posterior portion. When adjustment knob 630 is moved, it disengages one of first face clutch 651 and second face clutch 652, allowing for torque to transmit to only one of first clutch 655 and second clutch 656. As described above, since first clutch 655 is directly connected to outer driver 610, and second clutch 656 is directly connected to inner driver 620, rotation of only one of first face clutch 651 and second face clutch 652 will result in rotation of only one of outer driver 610 and inner driver 620. Each of outer driver 610 and inner driver 620 are configured to adjust one of the anterior portion or the posterior portion of expandable spinal fusion implant 300.

Figure 31:
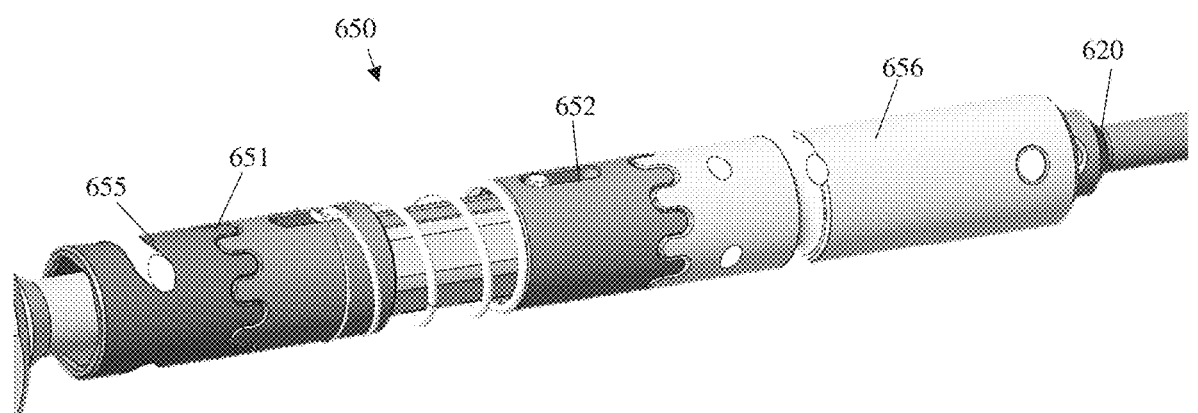
FIG. 31 shows the clutch mechanism of the expansion driver.

FIG. 31 shows the inner components of clutch 650, with the outer driver 610 removed for convenience. As illustrated, clutch 650 may include first face clutch 651, second face clutch 652, first clutch 655, and second clutch 656.

Figure 32:
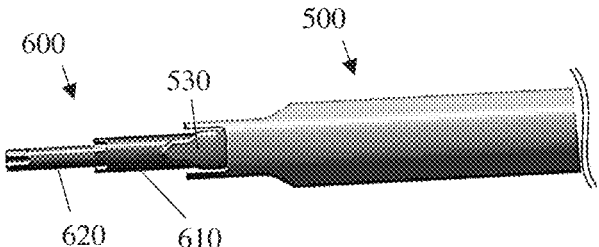
FIG. 32 shows a side view of the tip of the inserter having an expansion driver extending therethrough.

FIG. 32 shows the tip of inserter 500 with a tip of expansion driver 600 extending therefrom. Specifically, outer driver 610 and inner driver 620 are shown protruding from the tip of inserter 500.

Figure 33:
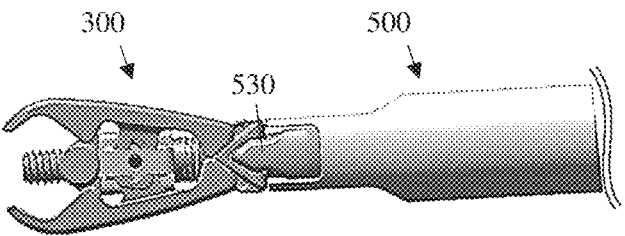
FIG. 33 shows a side view of the tip of the inserter having an expandable spinal fusion implant removably secured to a tip thereof.

FIG. 33 shows an expandable spinal fusion implant 300 removably secured to the tip of inserter 500, by arms 530 of inserter 500. Outer driver 610 of expansion driver 600 is configured to engage with first lead screw 335 of expandable implant 300, and inner driver 620 of expansion driver 600 is configured to extend through the hollow portion of first lead screw 335 and engage with second lead screw 336 of expandable implant 300.

Figure 34:
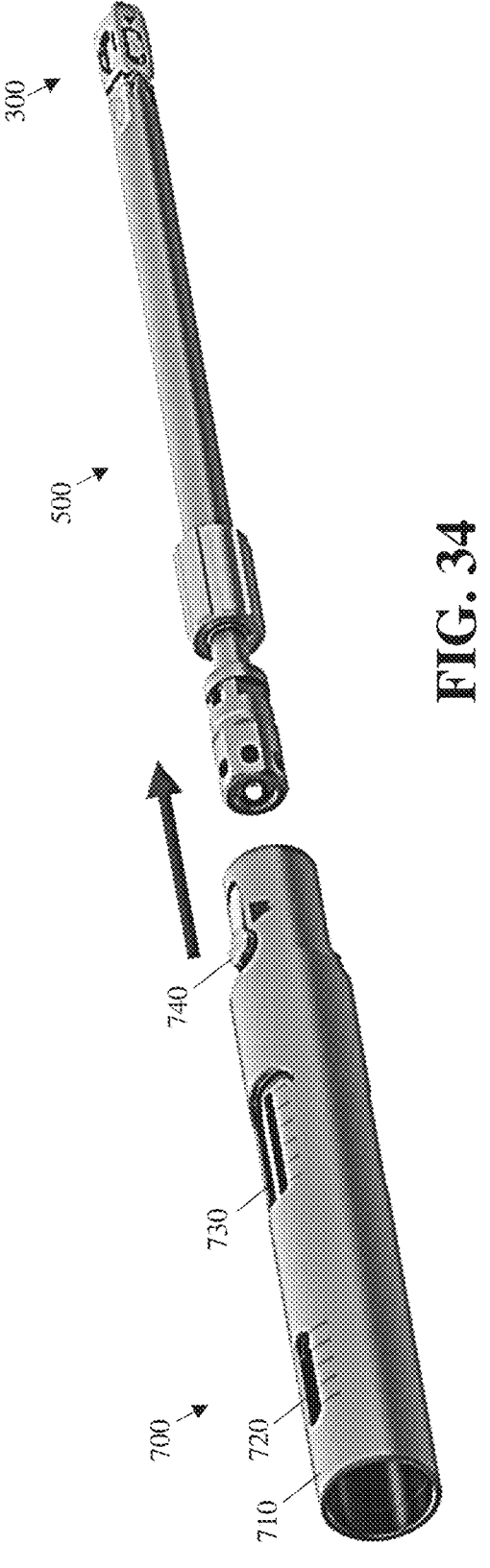
FIG. 34 shows an indicator handle being removably attached to the inserter.
Figures 35, 36:
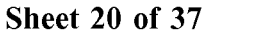
FIG. 35 shows a top view of the inserter removably attached to the expansion driver and the indicator handle.
FIG. 36 shows a top view of the inserter removably attached to the expansion driver and the indicator handle having an expandable spinal fusion implant removably secured to a tip thereof.
Figures 37, 38:
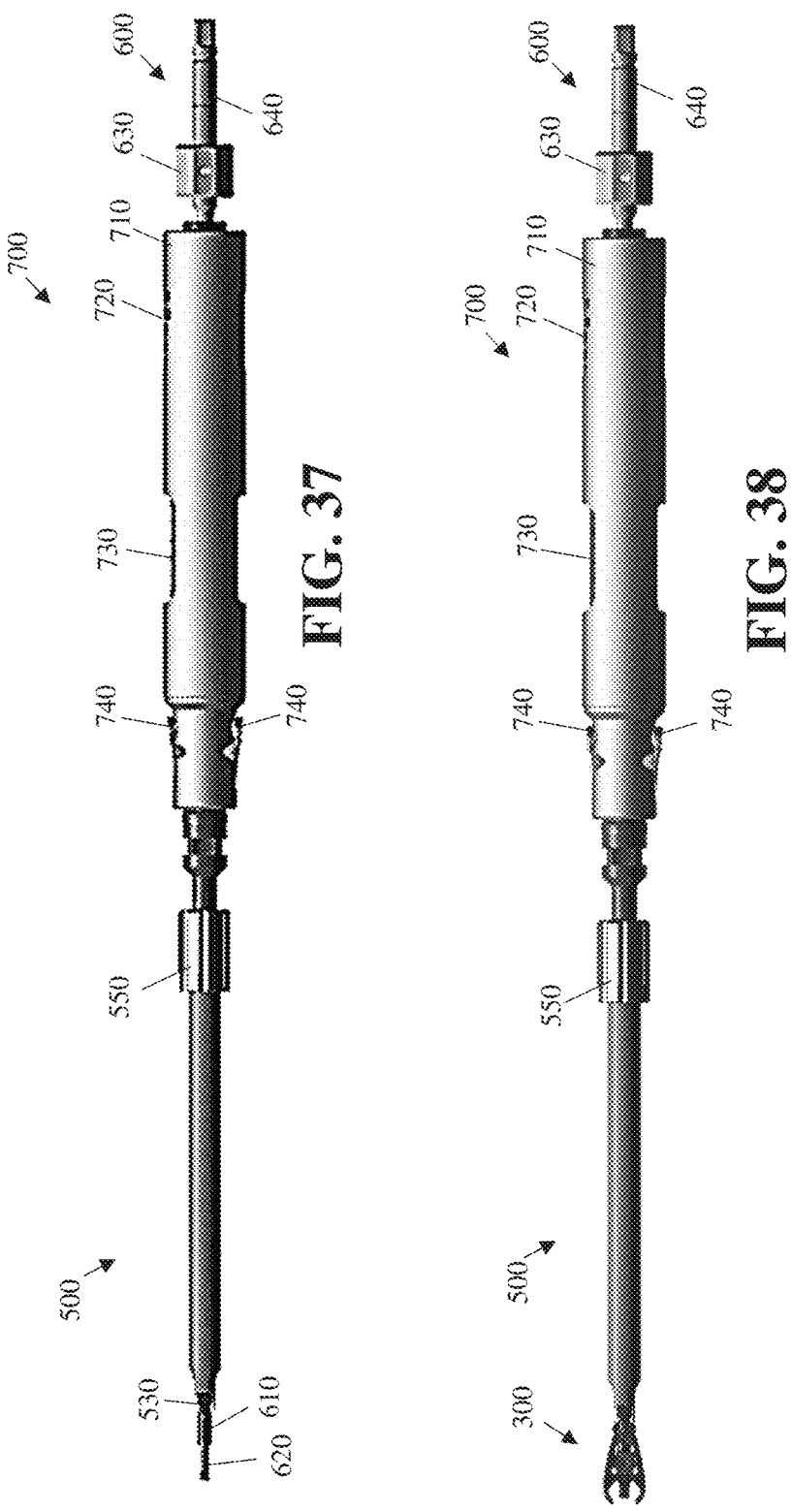
FIG. 37 shows a side view of the inserter removably attached to the expansion driver and the indicator handle.
FIG. 38 shows a side view of the inserter removably attached to the expansion driver and the indicator handle having an expandable spinal fusion implant removably secured to a tip thereof.

FIG. 34 shows an indicator handle 700 being provided to inserter 500. The indicator handle 700 includes a housing 710 configured to mate, for example telescopically, with inserter 500. In particular, a distal end of housing 710 may be configured to receive and clip onto a proximal end of inserter 500 via a button interface 740. Housing 710 includes a first indicator display 720 and a second indicator display 730. First indicator display 720 and second indicator display 730 are configured to display information about a current state of expandable spinal fusion implant 300. For example, in the embodiment illustrated in FIG. 34, first indicator display 720 is configured to communicate to the surgeon a height of the proximal end of expandable spinal fusion implant 300, and second indicator display 730 is configured to communicate to the surgeon an angle of lordosis of expandable spinal fusion implant 300.

A distal end of indicator handle 700 snaps onto inserter 500 via button interface 740. Indicator handle 700 may include a plurality of moving scales disposed therein which provide real-time expansion information regarding expandable spinal fusion implant 300. The first scale 735 may measure posterior height of expandable spinal fusion implant 300, while second scale 736 may be configured to measure lordosis of expandable spinal fusion implant 300. An increase in posterior height of implant 300 may be configured to cause a decrease in lordosis as described herein, so the readings for lordosis should be measured on the first scale 735. If the expandable spinal fusion implant 300 was at 12° of lordosis and the surgeon subsequently actuates the posterior segment of expandable spinal fusion implant 300, the first scale 735 would move, showing an indication of additional posterior height, while simultaneously moving the scale for lordosis.

FIGS. 35-38 show various views of the inserter assembly including inserter 500, expansion driver 600, and indicator handle 700. As discussed above, indicator handle 700 snaps onto inserter 500, with both indicator handle 700 and inserter 500 being cannulated and configured to receive outer driver 610 and inner driver 620 of the expansion driver 600 therethrough.

Figure 39:
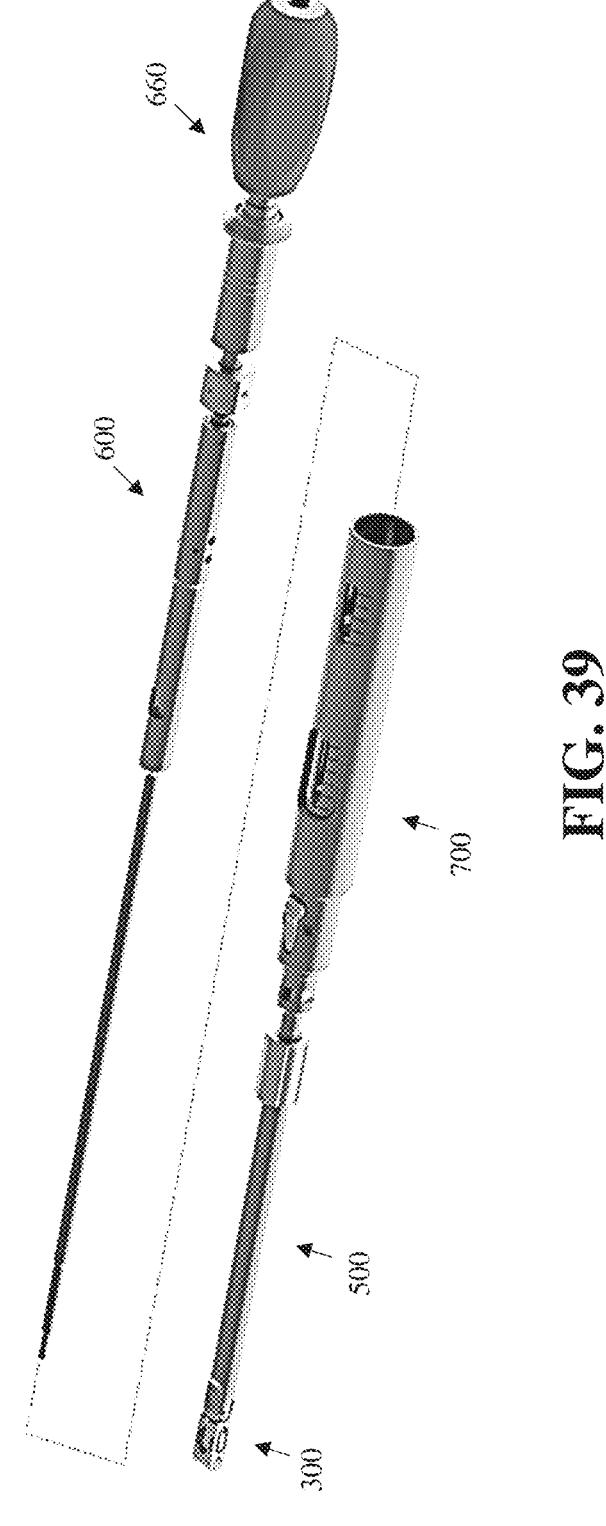
FIG. 39 shows an exploded perspective view of the expansion mechanism being inserted into the inserter having the indicator handle removably coupled thereto.

FIG. 39 shows the expansion driver 600 removably connected to a torque handle 660, with expansion driver 600 being fed down through indicator handle 700, and through inserter 500, such that a distal end of expansion driver 600 is in communication with the expandable spinal fusion implant 300.

Figure 40:
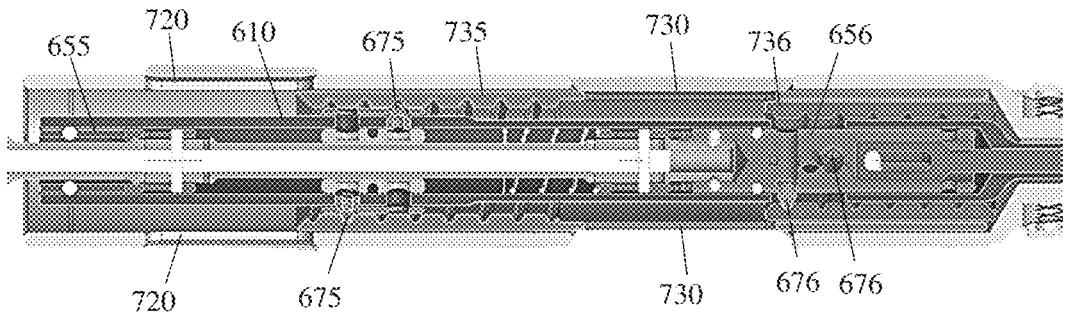
FIG. 40 shows a cross-sectional view the indicator handle having the expansion mechanism extending therethrough.

Turning to FIG. 40, an enhanced cross-sectional view of the expansion driver 600 is shown disposed within indicator handle 700. FIG. 40 illustrates the function of first indicator display 720 and second indicator display 730. Expansion driver 600 includes a first set of spring pins 675 and a second set of spring pins 676. Pins 675, 676 may be spring loaded. Spring pins 675, 676 may be shaped and spaced from each other in such a way that the spring pins 675, 676 engage internal threads of first scale 735 and second scale 736 within indicator handle 700. Since the pins 675, 676 are spring loaded, expansion driver 600 is configured to be removeably secured to indicator handle 700, with the spring pins 675, 676 configured to snap into place in the threads of the scales 735, 736 once in position.

The first set of spring pins 675 are connected to the posterior clutch 655, which is directly related to posterior height expansion of the expandable spinal fusion implant 300. As expansion driver 600 is torqued for selective posterior expansion, the first set of spring pins 675 threadingly communicate with first scale 735 to slide first scale 735 relative to indicator housing 710. Relative position of first scale 735 is indicated by first indicator display 720 and corresponds to an amount of adjustment of expandable spinal fusion implant 300.

Figure 41:
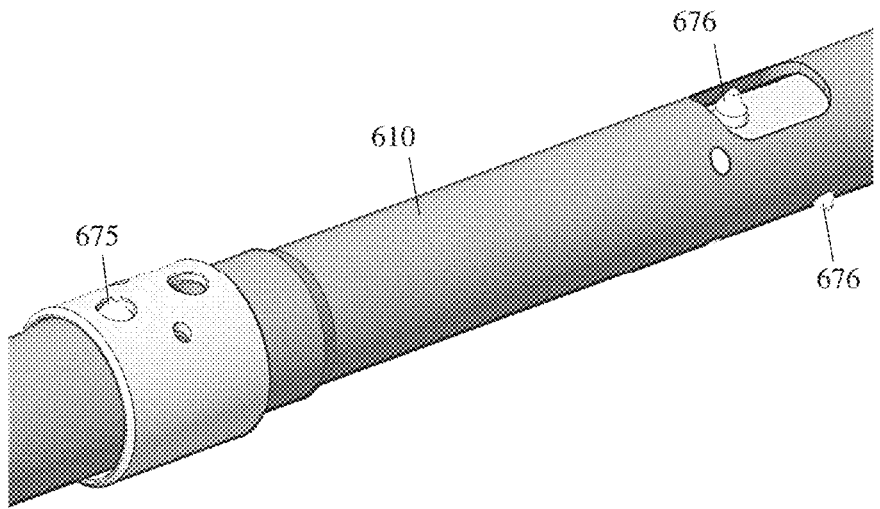
FIG. 41 shows an enhanced perspective view of the expansion mechanism to show the indicator guide pins.

The second set of spring pins 676 are connected to anterior clutch 656, which is directly related to anterior height expansion of the expandable spinal fusion implant 300. As expansion driver 600 is torqued for selective anterior expansion, second set of spring pins 676 threadingly communicate with second scale 736. Note that at least a portion of anterior clutch 656 is covered by outer driver 610. Outer driver 610 includes a through-slot which allows one to two of the second set of spring pins 676 to extend radially outward beyond outer driver 610 to engage second scale 736. FIG. 41 shows spring pins 675, 676 of expansion driver 600 extending out of outer driver 610.

In use, when expandable spinal fusion implant 300 is expanded in height (i.e., simultaneous anterior and posterior adjustment), first scale 735 and second scale 736 move together at the same time showing posterior height expansion but no increase in lordosis.

Figures 42, 43, 44:
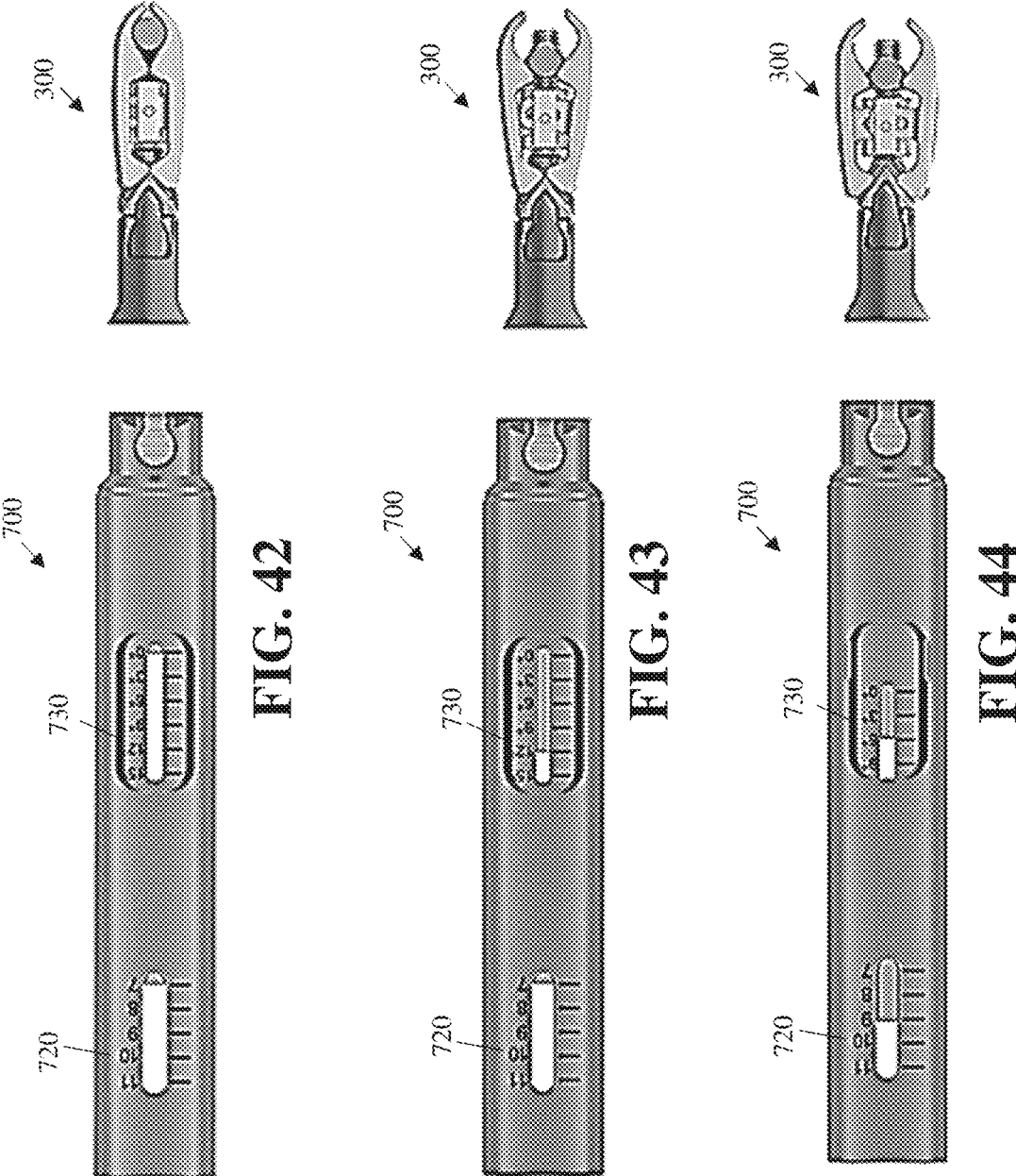
FIG. 42 shows an expandable spinal fusion implant in a collapsed configuration and the corresponding readings on the indicator displays of the indicator handle.
FIG. 43 shows an expandable spinal fusion implant expanded to an angle of lordosis and the corresponding readings on the indicator displays of the indicator handle.
FIG. 44 shows an expandable spinal fusion implant expanded to an expanded height and the corresponding readings on the indicator displays of the indicator handle.

FIGS. 42-44 show three adjustment states of expandable spinal fusion implant 300, and corresponding readings on first indicator display 720 and second indicator display 730. FIG. 42 shows expandable spinal fusion implant 300 in a collapsed configuration with first indicator display 720 reading 7 mm and second indicator display 730 reading 0° lordosis. Upon a selection by the surgeon to adjust for angle of lordosis on expansion driver 600, expansion driver 600 is configured to rotate inner driver 620, which rotates second lead screw 336 of expandable spinal fusion implant 300. Rotation of second lead screw 336 of expandable spinal fusion implant 300 is configured to cause threaded barrel 332 to move, and change an angle between first endplate 310 and second endplate 320 (FIGS. 18-20), thereby adjusting the anterior side of the implant 300 to set a desired angle of lordosis.

FIG. 43 shows an expandable spinal fusion implant 300 expanded to an angle of lordosis. First indicator display 720 reads 7 mm, and second indicator display 730 reads 12° lordosis. Upon selection by the surgeon to adjust the posterior side of expandable spinal fusion implant 300 on expansion driver 600, expansion driver 600 is configured to rotate outer driver 610, which is further configured to rotate first lead screw 335 of expandable spinal fusion implant 300. Rotation of first lead screw 335 of expandable spinal fusion implant 300 is configured to cause wedge 331 to move first endplate 310 relative to second endplate 320, thereby adjusting the posterior side of the implant 300 to set a desired height.

FIG. 44 shows an expandable spinal fusion implant 300 expanded to an expanded height. First indicator display 720 reads 9 mm, and second indicator display 730 reads 6° lordosis. Adjustment has increased the height of the posterior side of the expandable spinal fusion implant 300 and simultaneously reduced the angle of lordosis.

Figures 57, 58, 59:
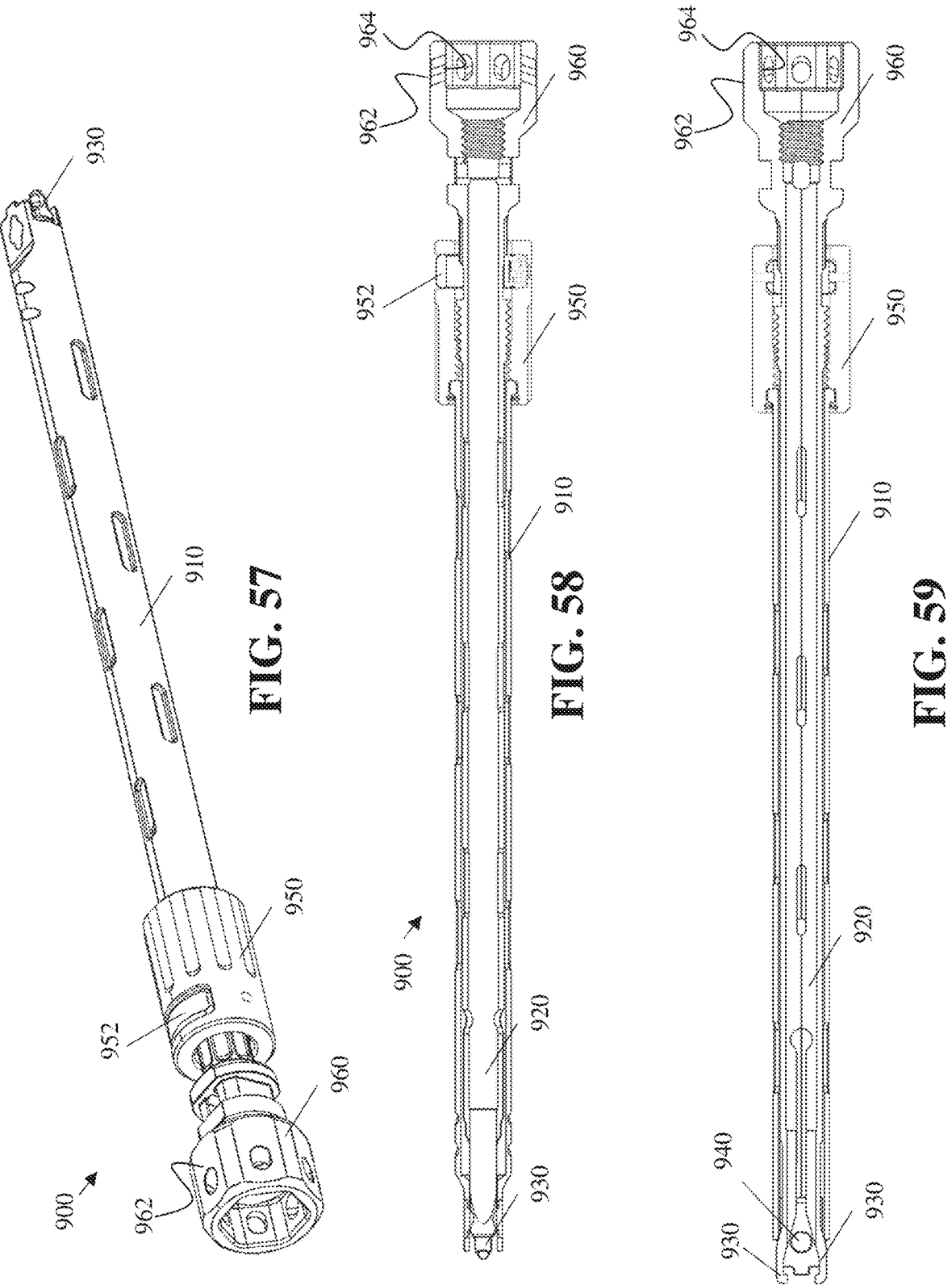
FIG. 57 shows a perspective view of an inserter according to an embodiment of the disclosure.
FIG. 58 shows a cross-sectional side view of the inserter of FIG. 57.
FIG. 59 shows a cross-sectional top view of the inserter of FIG. 57.
Figure 60:
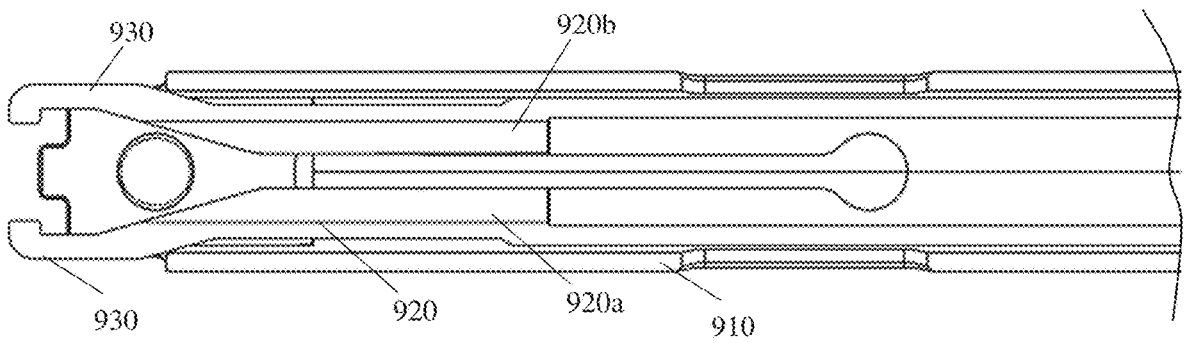
FIG. 60 shows an enlarged cross-sectional top view of the distal end of the inserter of FIG. 57.
Figure 61:
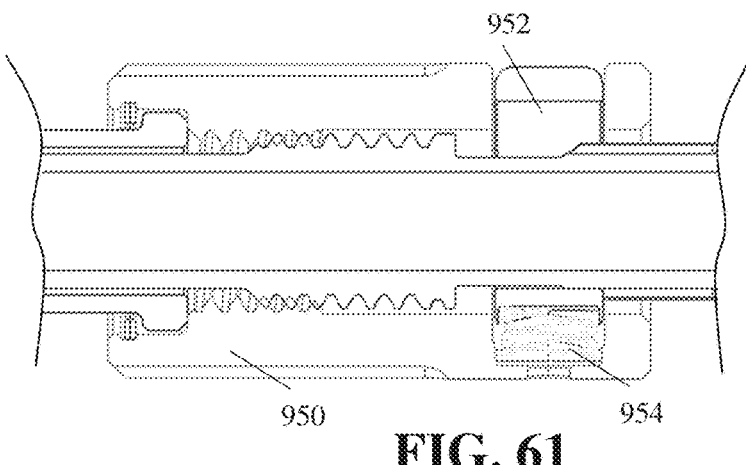
FIG. 61 shows an enlarged cross-sectional side view of the rotating thumbwheel of the insert of FIG. 57.

FIGS. 57-59 show another embodiment of an inserter 900 according to embodiments of the disclosure. In this embodiment, inserter 900 is substantially similar to inserter 500. Like inserter 500, inserter 900 may be used to place an expandable spinal fusion implant into the intervertebral disc space of a patient during surgery. The inserter 900 includes an outer shaft 910, an inner shaft 920, and two arms 930 configured to splay open when outer shaft 910 is drawn back, i.e. moved proximally, and to close when outer shaft 910 is pushed forward, i.e. distally toward the implant (not shown in FIGS. 57-59).

In this embodiment, inner shaft 920 has a distal geometry that splits inner shaft 920 into two halves 920a, 920b (FIG. 60) similar to a living hinge. Inner shaft 920 may be formed with arms 930 at a distal end thereof. Inserter 900 may also include a rotating thumbwheel 950 that actuates movement of outer shaft 910 relative to inner shaft 920. Rotation of thumbwheel 950 in one direction (e.g., clockwise or counter-clockwise) enables outer shaft 910 to be drawn back, i.e. proximally, thereby causing arms 930 to splay open, and rotation of thumbwheel 950 in the other direction (the other one of clockwise or counter-clockwise) enables outer shaft 910 to be pushed distally toward the implant (not shown), thereby causing arms 930 to close. Arms 930 can be splayed open when outer shaft 910 is drawn back, and button 940 disposed on the outer shaft 910 engages the ramps on the inside of arms 930. Arms 930 are urged closed when outer shaft 910 is pushed forward, clamping the arms 910 together. In this embodiment, thumbwheel 950 may include a spring-loaded button 952 (FIG. 61) and spring 954 (FIG. 62) configured to bias the spring-loaded button 952. Spring-loaded button 952 ratchets about inner shaft 920 and provides resistance to thumbwheel 950, thereby preventing accidentally movement of thumbwheel 950 during use. Spring-loaded button 952 also serves as a release to enable disassembly of inserter 900 for cleaning.

Referring to FIGS. 57-59, inserter 900 may include a connector 960 at a proximal end thereof. Connector 960 has a keyed outer surface 962 and a keyed inner surface 964. The keyed outer surface 962 is configured to couple with the indicator handle 1200 as will be described herein. The keyed inner surface 964 is configured to receive the expansion driver 1000 (FIGS. 62-64).

Figures 62, 63, 64:
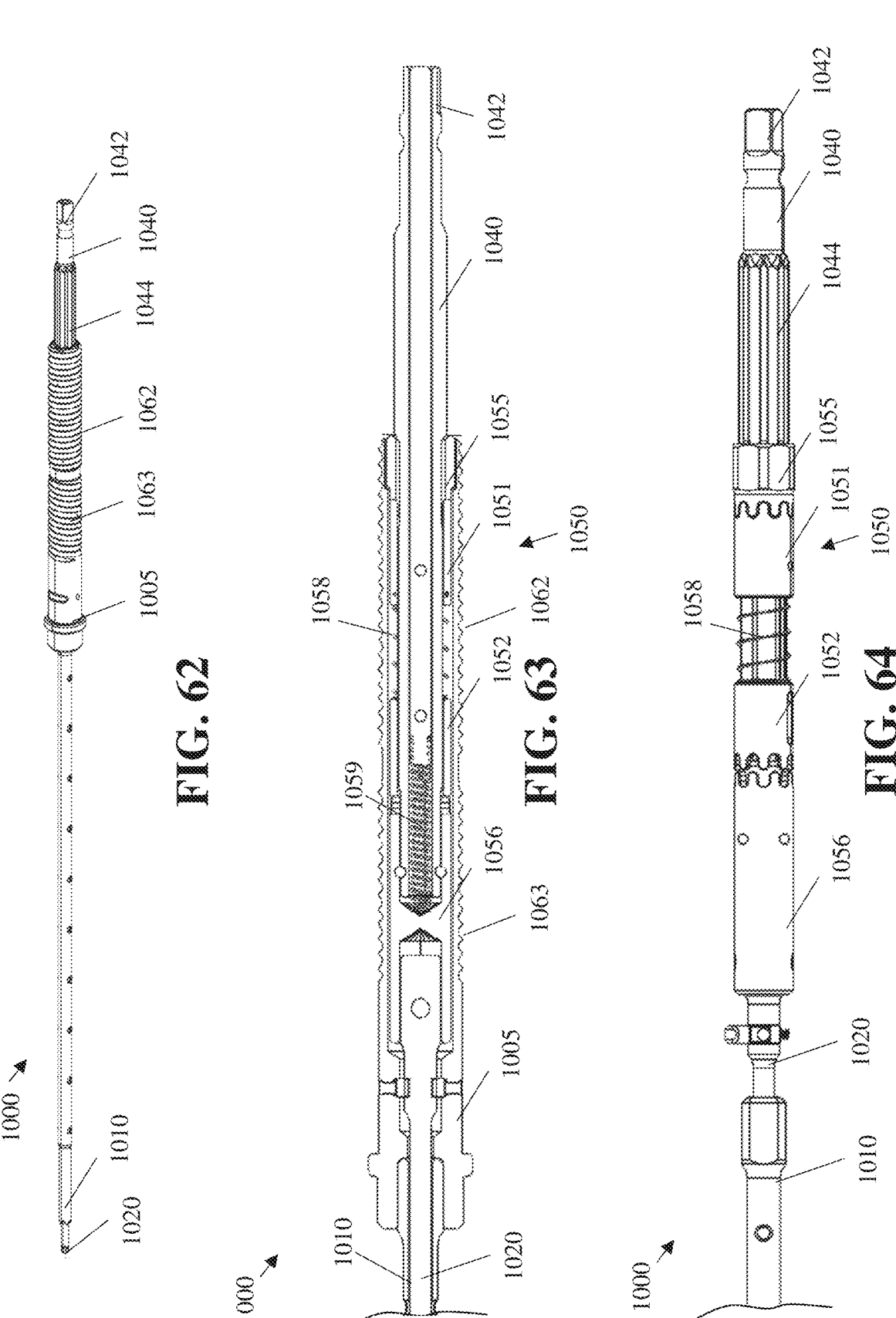
FIG. 62 shows a perspective view of an expansion driver according to an embodiment of the disclosure.
FIG. 63 shows a cross-sectional side view of the clutch mechanism of the expansion driver of FIG. 62.
FIG. 64 shows a side view of the clutch mechanism of the expansion driver of FIG. 62.

FIGS. 62-64 show another embodiment of an expansion driver 1000 according to aspects of the disclosure. In this embodiment, at least a portion of expansion driver 1000 is configured to pass through a hollow cavity of inserter 900 and engage with a first lead screw 835, and a second lead screw 836 of the expandable spinal fusion implant 800. In some embodiments, however, expansion driver 1000 can be used to expand expandable spinal fusion implant 800 without the use of inserter 900. Expansion driver 1000 includes an outer sleeve 1005, an inner driver 1020, an outer driver 1010, and a clutch 1050 positioned with the sleeve 1005. In this embodiment, inner driver 1020 is a hexalobe driver and outer driver 1010 is a crown driver. Inner driver 1020 is configured to expand the anterior portion of expandable spinal fusion implant 800 by rotating second lead screw 836. Second lead screw 836 may be configured to move first endplate 810 relative to second endplate 820 as described above. Inner driver 1020 extends within outer driver 1010 and through first lead screw 835 to couple with second lead screw 836. Outer driver 1010 is configured to expand the posterior portion of expandable spinal fusion implant 800 by rotating first lead screw 835. First lead screw 835 may be configured to move first endplate 810 relative to second endplate 820 as described above. When inner driver 1020 and outer driver 1010 are actuated together, expandable spinal fusion implant 800 expands in height. When inner driver 1020 and outer driver 1010 are actuated separately, an angle of lordosis is adjusted.

Inserter 900 and expansion driver 1000 provide a full range of adjustment of expandable spinal fusion implant 800 with a single, easy to use instrument, configured to switch between expansion modes without being removed. Expansion driver 1000 may include an input shaft 1040 having a keyed end 1042 for mating with a complementary keyed surface within an opening of an adjustment handle 1100. This is configured to allow the surgeon to select an aspect(s) of expandable spinal fusion implant 800 to be actively expanded, i.e., anterior, posterior, or both anterior and posterior. In addition, input shaft 1040 includes a portion 1044 having a geometry such as, e.g., a keyed interface, a star-shaped cross-section, etc., configured to mate with a complementary geometry within indicator handle 1200 as will be described herein. The portion 1044 is positioned between keyed end 1042 and first clutch 1055 about input shaft 1040.

Turning to FIG. 63, in use, when a surgeon wishes to expand either an anterior portion, a posterior portion, or both the anterior portion and posterior portion of the expandable spinal fusion device, the surgeon rotates handle 1100. Handle 1100 may be coupled to expansion driver 1000 to activate a clutch mechanism 1050. Clutch mechanism 1050 includes a first face clutch 1051, a second face clutch 1052, a first clutch 1055, and a second clutch 1056. First face clutch 1051 may be coupled to input shaft 1040 such that first face clutch 1051 is configured to rotate with input shaft 1040 and translate relative to input shaft 1040. First face clutch 1051 may be configured to selectively engage first clutch 1055, with first clutch 1055 being configured to communicate with and rotate outer driver 1010. Specifically, first clutch 1055 includes a keyed outer interface that mates with an inner surface of sleeve 1005, such that when first clutch 1055 rotates, sleeve 1005 also rotates. Sleeve 1005 is rotatably coupled with outer driver 1010 via a keyed interface of outer driver 1010, interacting with a keyed inner surface of sleeve 1005. Therefore, when input shaft 1040 rotates and first face clutch 1051 is engaged with first clutch 1055, the first clutch 1055 and the outer sleeve 1005 also rotate, thereby causing outer driver 1010 to rotate and cause expansion of the posterior portion of expandable spinal fusion implant 800. The outer driver 1010 is configured to communicate rotation to first lead screw 835 of expandable spinal fusion implant 800.

Second face clutch 1052 is coupled to input shaft 1040 such that second face clutch 1052 is configured to rotate with input shaft 1040 and translate relative to input shaft 1040. Second face clutch 1052 may be configured to selectively engage second clutch 1056, with second clutch 1056 being configured to communicate with and rotate inner driver 1020. Specifically, second clutch 1056 is directly coupled with inner driver 1020, such that when second clutch 1056 rotates, inner driver 1020 rotates. Therefore, when input shaft 1040 rotates and second face clutch 1052 is engaged with second clutch 1056, second clutch 1056 also rotates, thereby causing inner driver 1020 to rotate and cause expansion of the anterior portion of expandable spinal fusion implant 800. Inner driver 1020 is configured to communicate rotation to second lead screw 836 of expandable spinal fusion implant 800.

If a surgeon wants to expand both the anterior portion and the posterior portion of expandable spinal fusion implant 800 simultaneously, rotation of handle 1100 activates clutch 1050 which allows first face clutch 1051 to engage first clutch 1055 and second face clutch 1052 to engage second clutch 1056. Thus, upon a rotation of input shaft 1040, torque is transmitted to first face clutch 1051 and second face clutch 1052, and in turn transmitted to first clutch 1055 and second clutch 1056. First clutch 1055 is connected to outer driver 1010 via sleeve 1005, and second clutch 1056 is directly connected to inner driver 1020. Therefore, rotation of input shaft 1040 will result in actuation of both the anterior portion and the posterior portion of expandable spinal fusion implant 800.

To selectively adjust either the anterior portion or the posterior portion of expandable spinal fusion implant 800, the surgeon may actuate handle 1100 to select a particular mode of adjustment for selective expansion of the anterior portion or the posterior portion. Actuation of handle 1100 causes input shaft 1040 to interact with first spring 1058 and second spring 1059 to selectively cause engagement of first face clutch 1051 with first clutch 1055 and second face clutch 1052 with second clutch 1056, thereby enabling rotation of only one of outer driver 1010 and inner driver 1020. That is, handle 1100 can be actuated between three modes. In a first mode, first and second face clutches 1051, 1052 each engage with first and second clutches 1055, 1056, respectively, thereby enabling expansion of both the anterior portion and posterior portion of expandable spinal fusion implant 800. In a second mode, first face clutch 1051 engages with first clutch 1055 but second face clutch 1052 does not engage with second clutch 1056, thereby enabling expansion of only the posterior portion of expandable spinal fusion implant 800. In a third mode, second face clutch 1052 engages with second clutch 1056 but first face clutch 1051 does not engage with first clutch 1055, thereby enabling expansion of only the anterior portion of expandable spinal fusion implant 800.

Outer sleeve 1005 includes a first outer threaded portion 1062 and a second outer threaded portion 1063. As will be described herein, the first and second threaded portions 1062, 1063 interact with ball bearings within the indicator handle 1200 as will be described herein.

Figures 65, 66, 67:
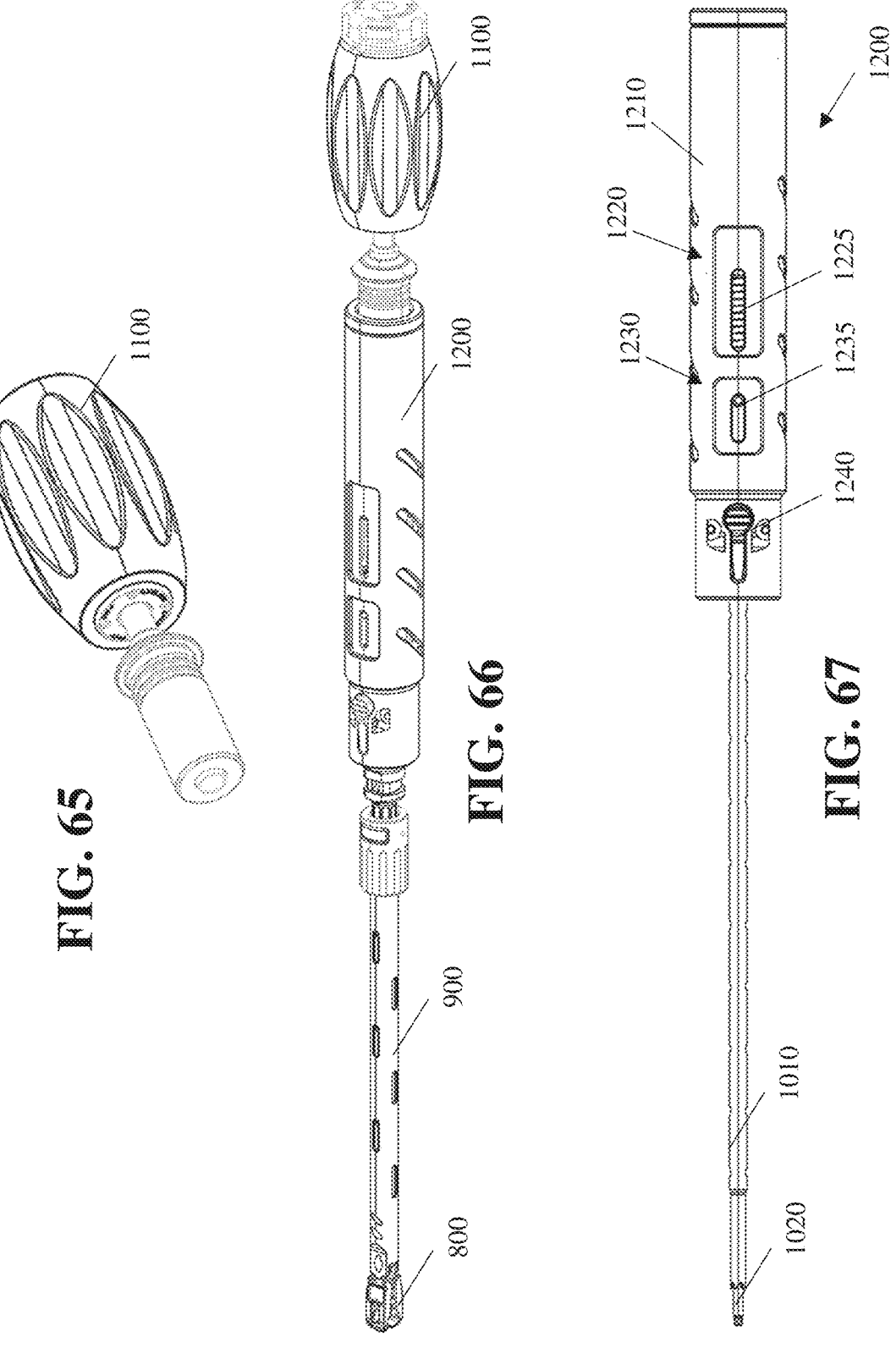
FIG. 65 shows a perspective view of an adjustment handle according to an embodiment of the disclosure.
FIG. 66 shows a perspective view of an assembly including the expandable spinal fusion implant, the inserter, the indicator handle, the expansion driver, and adjustment handle according to an embodiment of the disclosure.
FIG. 67 shows a top view of the indicator handle coupled with the expansion driver according to an embodiment of the disclosure.

FIG. 66 shows an assembly including expandable spinal fusion implant 800, inserter 900, adjustment handle 1100, and an indicator handle 1200. As shown, inserter 900 is coupled to expandable spinal fusion implant 800. Inserter 900 can be coupled to expandable spinal fusion implant 800 as described herein relative to inserter 500 and expandable spinal fusion implant 300. Further, indicator handle 1200 is shown coupled with inserter 900. Indicator handle 1200 can be coupled to inserter 900 as described herein relative to inserter 500 and indicator handle 700. Expansion driver 1000, not labeled in FIG. 66, is positioned within inserter 900 and indicator handle 700, with handle 1100 coupled to an end of expansion driver 1000 extending about the assembly opposite expandable spinal fusion implant 800.

Indicator handle 1200 is substantially similar to indicator handle 700, and includes a housing 1210 configured to mate with, e.g., telescopically receive and clip onto, a proximal end of inserter 900 via a button interface 1240 (FIG. 67). Housing 1210 includes a first indicator display 1220 and a second indicator display 1230. First indicator display 1220 and second indicator display 1230 are configured to display information about a current state of expandable spinal fusion implant 800. For example, in the illustrated embodiment, first indicator display 1220 is configured to communicate to the surgeon a height of the anterior end of expandable spinal fusion implant 800, and second indicator display 1230 is configured to communicate to the surgeon a height of the posterior end of expandable spinal fusion implant 800.

A distal end of indicator handle 1200 may be configured to snap onto inserter 900 via a button interface 1240. Indicator handle 1200 has a plurality of moving scales disposed therein which provide real-time expansion information regarding the state of expandable spinal fusion implant 800. First scale 1225 measures anterior height of expandable spinal fusion implant 800, while second scale 1235 is configured to measure posterior height of expandable spinal fusion implant 800.

Figure 68:
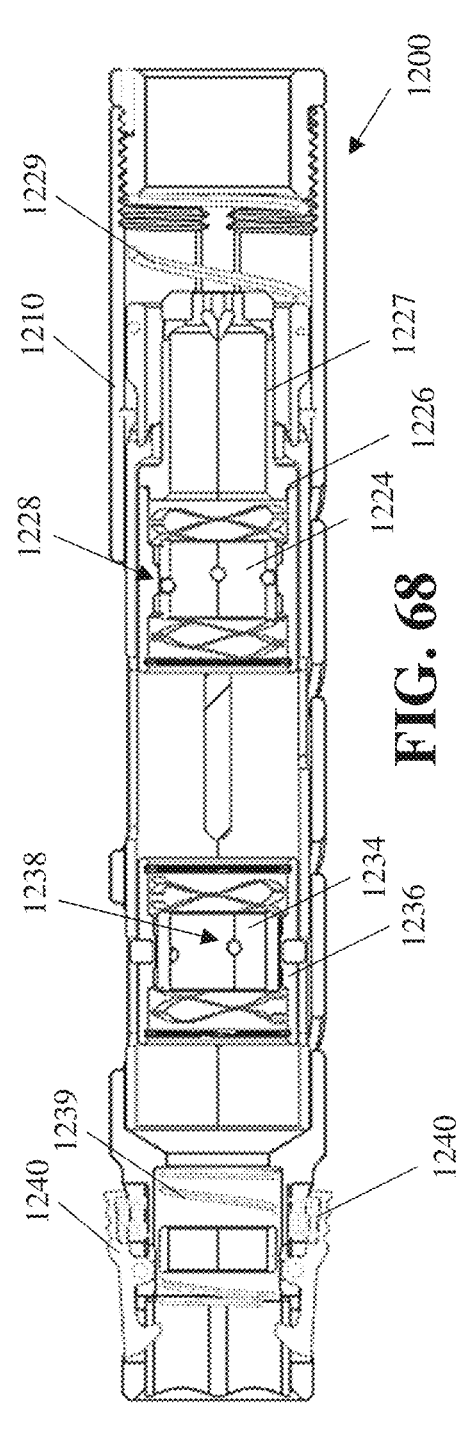
FIG. 68 shows a cross-sectional view of the indicator handle.
Figure 69:
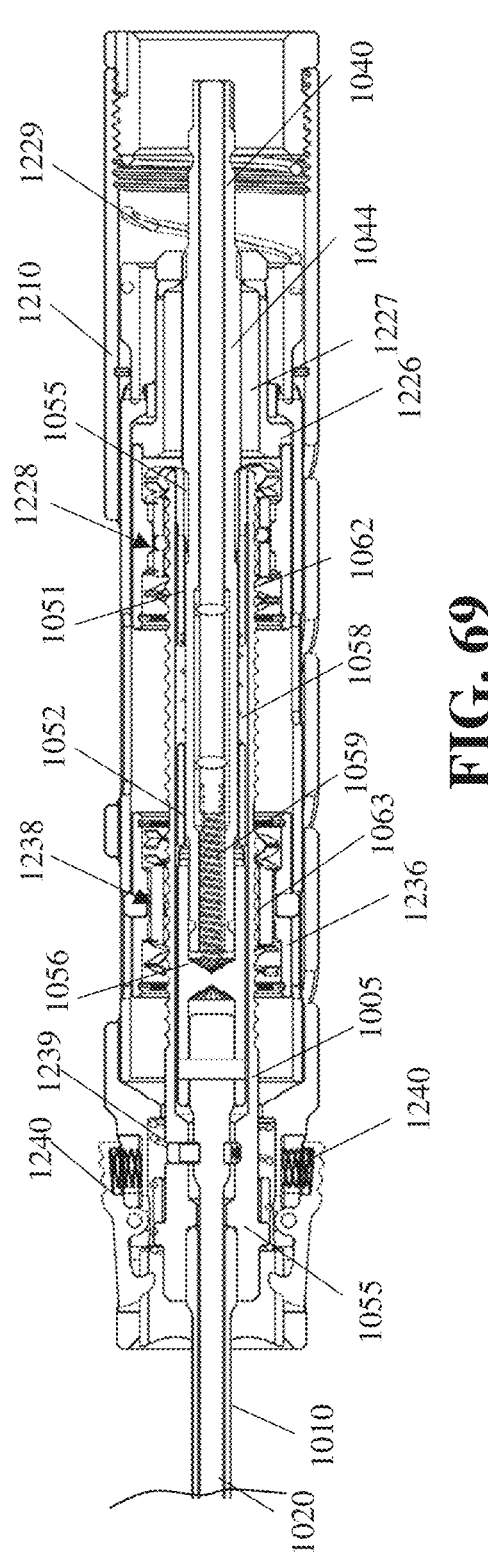
FIG. 69 shows a cross-sectional view of the indicator handle coupled with the expansion driver.

FIG. 68 shows a cross-sectional view of indicator handle 1200. As shown, indicator handle 1200 differs from indicator handle 700 in that indicator handle 1200 includes a first inner sleeve 1224, a first outer sleeve 1226, a second inner sleeve 1234, and a second outer sleeve 1236. First outer sleeve 1226 substantially surrounds first inner sleeve 1224. Second outer sleeve 1236 substantially surrounds second inner sleeve 1234. The inner sleeves 1224, 1234 have outer geometries that complement inner geometries of outer sleeves 1226, 1236, respectively, at least where inner sleeves 1224, 1234 sit within outer sleeves 1226, 1236. First outer sleeve 1226 includes a portion 1227 having an inner geometry (e.g., a keyed interface, a star-shaped cross-section, etc.) configured to mate with a complementary geometry of the portion 1044 (FIGS. 62 and 64) of input shaft 1040 (FIGS. 62-64). Thus, first outer sleeve 1226 is coupled to input shaft 1040 in a manner configured to cause first outer sleeve 1226 to rotate with input shaft 1040, while being able to translate relative to input shaft 1040. As a result, when input shaft 1040 is rotated, first outer sleeve 1226 rotates.

First inner sleeve 1224 includes a first ball bearing 1228 having a plurality of balls disposed between first sleeve 1226 and sleeve 1005 (FIGS. 62-63) when expansion driver 1000 (FIGS. 62-64) is positioned within indicator handle 1200. Second inner sleeve 1234 includes second ball bearing 1238 having a plurality of balls disposed between second sleeve 1236 and sleeve 1005 when expansion driver 1000 (FIGS. 62-64) is positioned within indicator handle 1200.

These sleeves 1224, 1226, 1234, 1236 and ball bearings 1228, 1238 provide an alternative to the spring pins 675, 676 for moving the scales 1225, 1235. The balls of the ball bearings 1228, 1238 interact with the outer threaded portions 1062, 1063 of the sleeve 1005 of expansion driver 1000, such that the balls of ball bearings 1228, 1238 move within the grooves of the threads within outer threaded portions 1062, 1063 to cause movement of scales 1225, 1235. The spacing of the balls of ball bearings 1228, 1238 matches the pitch of the threads of the outer threaded portions 1062, 1063 of sleeve 1005 of expansion driver 1000.

The first ball bearing 1228 sits within the outer threaded portion 1062 of sleeve 1005 and relates to first scale 1225, thereby communicating a height of the anterior portion of implant 800 to the surgeon. The second ball bearing 1238 sits within the outer threaded portion 1063 of sleeve 1005 and relates to second scale 1235, thereby communicating a height of the posterior portion of implant 800 to the surgeon. If expandable spinal fusion implant 800 is expanding both anterior and posterior portions of the implant 800 simultaneously, the first scale 1235 and the second scale 1236 move together at the same time showing both posterior and anterior height adjustment.

More specifically, as discussed herein, the portion 1227 of first outer sleeve 1226 includes a geometry complementary to the geometry of portion 1044 of input shaft 1040 of expansion driver 1000. In order to expand implant 800, handle 1100 is actuated and input shaft 1040 rotates in one of three modes, i.e., to expand both the anterior and posterior ends of implant 800, to expand only the anterior portion of implant 800, or to expand only the posterior portion of implant 800. Regardless of which expansion mode is selected using handle 1100, input shaft 1040 is always rotated during expansion of implant 800. As a result, first sleeve 1226 always rotates during any of the three expansion modes, due to first sleeve 1226 being coupled to input shaft 1040 via complementary geometries of portion 1044 and portion 1227. While expansion driver 1000 can be used in any of three modes, indicator handle 1200 shows only anterior and posterior adjustment when expansion driver 1000 is used during individual anterior and posterior adjustment, not simultaneous anterior and posterior adjustment.

In order to expand only the posterior portion of implant 800, handle 1100 may be actuated by a user or surgeon, such that first face clutch 1051 engages first clutch 1055, thereby causing first clutch 1055 to rotate as input shaft 1040 rotates. However, second face clutch 1052 is not engaged with second clutch 1056 in this mode. Therefore, second clutch 1056 does not rotate with input shaft 1040. During rotation of first clutch 1055, sleeve 1005 of expansion driver 1000 also rotates. Because the balls of first ball bearing 1228 are positioned within the threaded portion 1062 of sleeve 1005, and both sleeve 1005 and first outer sleeve 1226 of indicator handle 1200 are rotating with input shaft 1040 in this mode, the balls of first ball bearing 1228 do not translate within the threaded portion 1062 of sleeve 1005. Therefore, no anterior height adjustment is shown on scale 1225. Because the balls of second ball bearing 1238 are positioned within the threaded portion 1063 of sleeve 1005, and sleeve 1005 is rotating with input shaft 1040 in this mode, the balls of second ball bearing 1238 move within the threaded portion 1063 of sleeve 1005. As a result, the scale 1235 moves to show a height adjustment of the posterior portion of implant 800.

In order to expand only the anterior portion of implant 800, handle 1100 may be actuated by a user or surgeon, such that second face clutch 1052 engages with second clutch 1056, thereby causing second clutch 1056 to rotate as input shaft 1040 rotates. However, first face clutch 1051 is not engaged with first clutch 1055 in this mode, and therefore, neither first clutch 1055 nor sleeve 1005 rotate with input shaft 1040. Because first outer sleeve 1226 of indicator handle 1200 always rotates with rotation of input shaft 1040, and sleeve 1005 of expansion driver 1000 does not rotate in this mode, the first ball bearing 1228 is caused to translate about sleeve 1005, thereby moving anterior scale 1225. In this mode, the second ball bearing 1238 does not move, and therefore, posterior scale 1235 does not show any adjustment.

The sleeves 1226, 1236 are biased via springs 1229, 1239, i.e., sleeves 1226, 1236 are spring-loaded. Therefore, sleeves 1226, 1236 allow indicator handle 1200 to ratchet over expansion driver 1000 until indicator handle 1200 attaches to inserter 1000.

Figure 70:
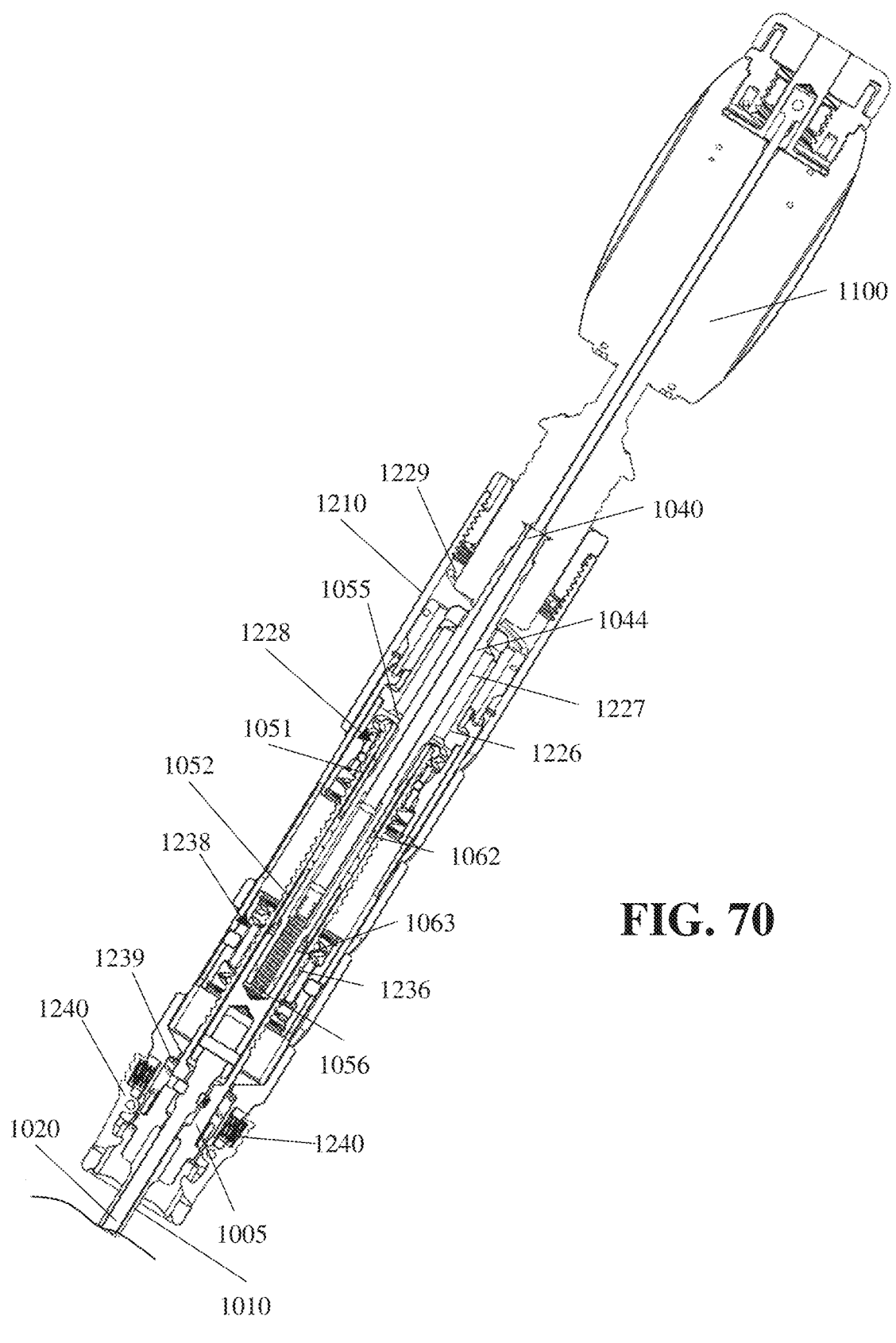
FIG. 70 shows a cross-sectional view of the indicator handle, the expansion driver, and the adjustment handle according to embodiments of the disclosure.
Figure 71:
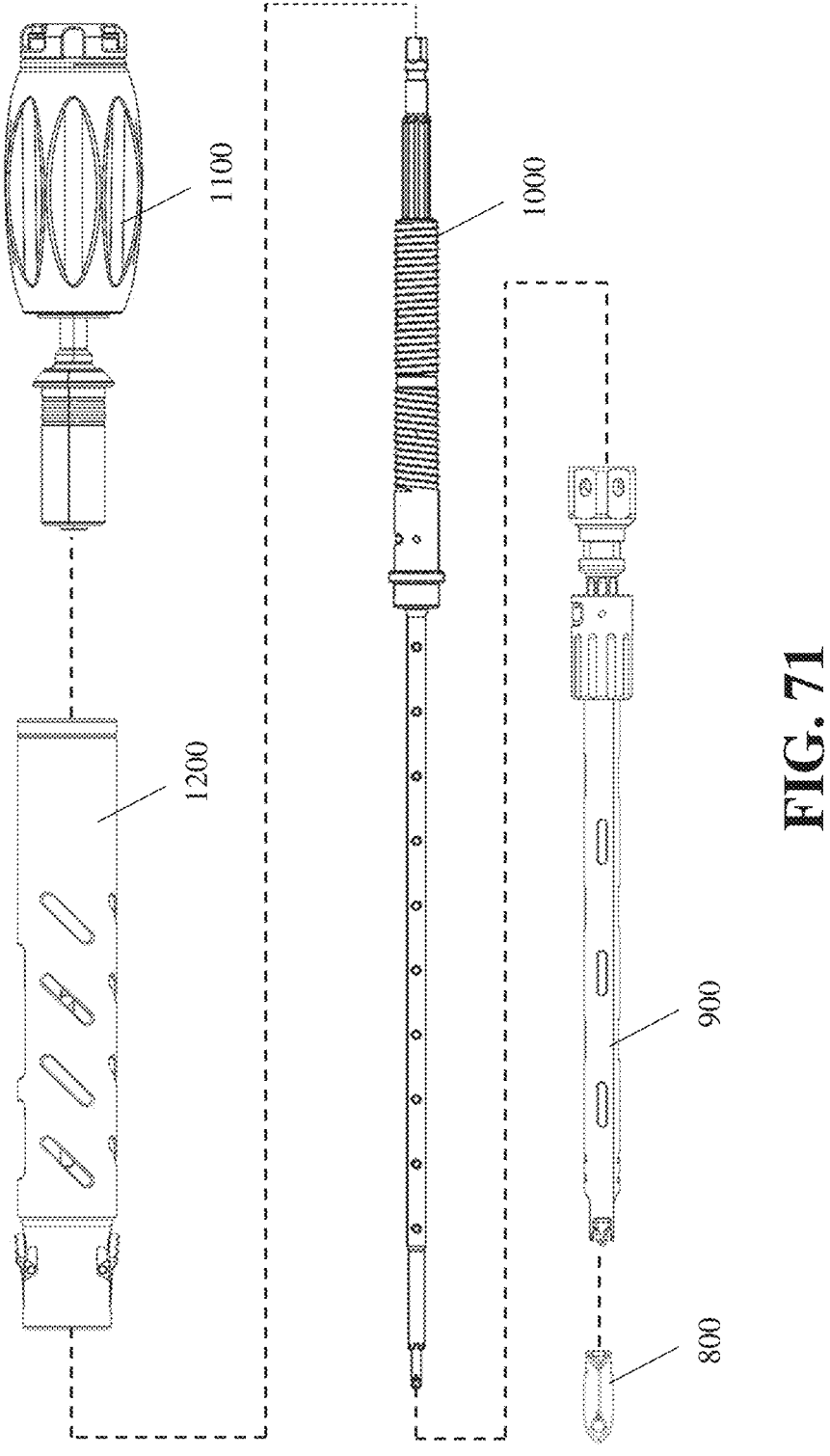
FIG. 71 shows a perspective view of the expansion mechanism being inserted into the inserter having the indicator handle and adjustment handle removably coupled thereto.

Turning to FIG. 70, to assemble the instrument, inserter 900 is first coupled to expandable spinal fusion implant 800 via arms 930 (FIGS. 57-60). Expansion driver 1000 is then introduced into inserter 900 such that drivers 1010, 1020 (FIGS. 62-64) couple with lead screws 825, 835 (FIGS. 45-52), respectively. Indicator handle 1200 is then provided over expansion driver 1000 such that button interfaces 1040 (FIGS. 66-69) snap onto inserter 900 and the balls of ball bearings 1028, 1038 (FIGS. 68-69) are seated within the outer threaded portions 1058, 1059 (FIGS. 62 and 69) of expansion driver 1000. Adjustment handle 1100 is then provided within indicator handle 1200 until handle 1100 couples with the keyed end 1042 (FIGS. 62-64) of expansion driver 1000.

In one exemplary method of use, an expandable spinal fusion implant 100, 200, 300, 400, 800 as disclosed herein may be proportioned to be introduced into a prepared intervertebral space of a patient to correct a spinal deformity. A medical practitioner may access an intervertebral disc space of a patient using a substantially lateral approach, or any other approach known and used in the art. The medical practitioner may prepare the area by removing the intervertebral disc of the patient. The medical practitioner may then introduce an expandable spinal fusion implant such as implant 100, 200, 300, 400, 800 in a first collapsed configuration using an insertion device 500, 900, and adjust the expandable spinal fusion implant device to a desired height and lordosis angle using the insertion device. The medical practitioner may observe at least one indicator display of an indicator handle of the insertion device 500, 900 to observe an amount of adjustment of the spinal fusion implant. Once the medical practitioner adjusts the implant 100, 200, 300, 400, 800 to a desired height and angle, for example lordosis angle between the first endplate and the second endplate, the medical practitioner may remove the inserter 500, 900 and complete the surgery.

A number of embodiments of the invention have been described. Nevertheless, it will be understood that various modifications may be made without departing from the spirit and scope of the invention. Accordingly, other embodiments are within the scope of the following claims.

What is claimed is:

1. An expandable implant device comprising:
a first endplate having a first linkage, a first ramp, and a first barrel contact surface;
a second endplate having a second linkage, a second ramp, and a second barrel contact surface;
a coupler at least partially disposed between the first endplate and the second endplate, wherein the coupler is configured to moveably connect the first endplate to the second endplate;
a first lead screw, having a first longitudinal axis extending longitudinally along a length of a shaft of the first lead screw, coupled to a second lead screw by the coupler, with the first lead screw configured to rotate independently of the second lead screw, wherein the first lead screw and the second lead screw are coaxial and a first end of the first lead screw is positioned adjacent to a second end of the second lead screw;
a passive locking mechanism at least partially disposed within the coupler, wherein the passive locking mechanism is configured to prevent unintentional rotation of the first lead screw and the second lead screw;
a wedge configured to translate along a length of the first lead screw as the first lead screw is rotated,
wherein the wedge is configured to communicate with the first ramp of the first endplate and the second ramp of the second endplate to displace the first endplate relative to the second endplate as the wedge translates along the first lead screw; and
a threaded barrel configured to translate along a length of the second lead screw as the second lead screw is rotated,
wherein the threaded barrel is configured to communicate with the first barrel contact surface of the first endplate and the second barrel contact surface of the second endplate as the threaded barrel translates along the second lead screw,
wherein a rotation of at least one of the first lead screw and the second lead screw is configured to change a dimension of the expandable implant device,
wherein the passive locking mechanism includes a deformable pin at least partially disposed within the coupler, and
wherein the deformable pin has a second longitudinal axis extending longitudinally along a length of the deformable pin, the second longitudinal axis extending generally parallel with the first longitudinal axis of the first lead screw when the deformable pin engages a head of the first lead screw to prevent unintentional rotation thereof.

2. The expandable implant device of claim 1, wherein the threaded barrel comprises a substantially circular endplate contact surface configured to communicate with the first barrel contact surface of the first end plate and the second barrel contact surf ace of the second endplate to move the first endplate and the second endplate as the threaded barrel is translated along the length of the second lead screw, and wherein the first endplate and the second endplate are configured to move relative to the coupler.

3. The expandable implant device of claim 1, wherein the dimension of the expandable implant device changed is a height.

4. The expandable implant device of claim 1, wherein the dimension of the expandable implant device changed is an angle between the first endplate and the second endplate.

5. The expandable implant device of claim 1, wherein the dimension of the expandable implant device changed is both a height and an angle between the first endplate and the second endplate.

6. The expandable implant device of claim 1, wherein rotation of the first lead screw causes the wedge to translate along the first lead screw in a first direction, and wherein rotation of the second lead screw causes the threaded barrel to translate along the second lead screw in a second direction opposite the first direction.

* * * * *